United States Patent
Brenner et al.

(10) Patent No.: US 7,488,478 B2
(45) Date of Patent: *Feb. 10, 2009

(54) METHODS AND COMPOSITIONS FOR TREATMENT OF INFLAMMATORY DISEASE USING CADHERIN-11 MODULATING AGENTS

(75) Inventors: Michael B. Brenner, Newton, MA (US); Xavier Valencia, Bethesda, MD (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/220,396

(22) Filed: Aug. 31, 2005

(65) Prior Publication Data

US 2006/0104972 A1  May 18, 2006

Related U.S. Application Data

(60) Continuation of application No. 10/457,257, filed on Jun. 9, 2003, now Pat. No. 6,964,768, which is a division of application No. 09/654,328, filed on Sep. 1, 2000, now Pat. No. 6,787,136.

(60) Provisional application No. 60/152,456, filed on Sep. 3, 1999, provisional application No. 60/153,490, filed on Sep. 13, 1999.

(51) Int. Cl.
*A61K 38/00* (2006.01)
*A61K 39/00* (2006.01)

(52) U.S. Cl. .................. 424/184.1; 424/192.1; 514/2
(58) Field of Classification Search .................. None
See application file for complete search history.

(56) References Cited

U.S. PATENT DOCUMENTS

| | | | |
|---|---|---|---|
| 5,597,725 A | 1/1997 | Suzuki | |
| 5,639,634 A | 6/1997 | Suzuki | |
| 5,646,250 A | 7/1997 | Suzuki | |
| 5,708,143 A | 1/1998 | Suzuki | |
| 5,798,224 A | 8/1998 | Suzuki | |
| 5,886,026 A * | 3/1999 | Hunter | |
| 6,086,877 A * | 7/2000 | Nishioka et al. | |
| 6,165,745 A * | 12/2000 | Ward et al. | |
| 6,433,149 B1 | 8/2002 | Blaschuk et al. | |
| 6,472,367 B1 | 10/2002 | Blaschuk et al. | |
| 6,787,136 B1 | 9/2004 | Brenner et al. | |
| 6,964,768 B2 | 11/2005 | Brenner et al. | |

FOREIGN PATENT DOCUMENTS

| | | |
|---|---|---|
| WO | WO 93/21302 A1 | 10/1993 |
| WO | WO 98/02452 A2 | 1/1998 |
| WO | WO 98/25946 A1 | 6/1998 |
| WO | WO 98/49560 * | 11/1998 |
| WO | WO 98/49560 A1 | 11/1998 |
| WO | WO 99/35166 A1 | 7/1999 |

OTHER PUBLICATIONS

Kuntz. Structure-based strategies for drug design and discovery. Science. 1992 257(5073):1078-1082.*

Miller et al Ligand binding to proteins: the binding landscape model. Protein Sci. Oct. 2007;6(10):2166-79.*

Branch AD. A good antisense molecule is hard to find. Trends Biochem Sci. Feb. 1998;23(2):45-50.*

Van Noort JM, Amor S. Cell biology of autoimmune diseases. Int Rev Cytol. 1998;178:127-206.*

Mountain A. Gene therapy: the first decade. Trends Biotechnol. Mar. 2000;18(3):119-28.*

Kahan BD. Immunosuppressive therapy. Curr Opin Immunol. 4(5):553-560, 1992.*

Ngo J.T, Marks J., Karplus M., Computational complexity, protein structure prediction, and the Levinthal paradox in The Protein Folding Problem, ch.14, pp. 491-494, Birkhauser, 1994.*

Hoffmann et al. Cloning and expression analysis of a novel mesodermally expressed cadherin. Dev Biol. May 1995;169(1):337-46.*

Valencia et al., Identification of cadherin-11 in type B synoviocytes derived from rheumatoid arthritis patients. Arthritis and Rheumatism. Sep. 1998;41(9):s190.

Branch et al., A good antisense molecule is hard to find. Trends Biochem Sci. Feb 1998;23(2):45-50.

Cepek et al., Integrin alpha E beta 7 mediates adhesion of T lymphocytes to epithelial cells. J Immunol. Apr. 15, 1993;150(8 Pt 1):3459-70.

Falcini et al., Cadherins expression in autoimmune diseases. Arthritis Rheum. 1997; Suppl 40: s283.

Hoffmann et al., Cloning and expression analysis of a novel mesodermally expressed cadherin. Dev Biol. May 1995;169(1):337-46.

Jorgensen et al., In vivo migration of radiolabelled lymphocytes in rheumatoid synovial tissue engrafted in SCID mice: implication of beta 2 and beta 7-integrin. J Rheumatol. Jan. 1996;23(1):32-5.

Kahan et al., Immunosuppressive therapy. Curr Opin Immunol. Oct. 1992;4(5):553-60.

(Continued)

*Primary Examiner*—Maher M Haddad
(74) *Attorney, Agent, or Firm*—Wolf, Greenfield & Sacks, P.C.

(57) ABSTRACT

A method for treating inflammatory joint diseases by inhibiting cadherin-11 mediated cellular function using a cadherin-11 modulating agent is provided. Also provided are screening assays for identifying pharmaceutical lead compounds capable of modulating cellular functions of cadherin-11 such as cell proliferation, apoptosis, factor secretion, and binding of cadherin-11 to cadherin-11 counter-receptor inhibiting binding of cadherin-11 to its counter-receptor either in the context of a cell or in soluble form.

7 Claims, 6 Drawing Sheets

OTHER PUBLICATIONS

Kiener et al.; Cadherin-11 induces rheumatoid arthritis fibroblast-like synoviocytes to form lining layers in vitro. Am J Pathol. May 2006;168(5):1486-99. Abstract Only.

MacCalman et al., Regulated expression of cadherin-11 in human epithelial cells: a role for cadherin-11 in trophoblast-endometrium interactions? Dev Dyn. Jun. 1996;206(2):201-11.

Mountain, Gene therapy: the first decade. Trends Biotechnol. Mar. 2000;18(3):119-28.

Ngo et al., Computational complexity, protein structure prediction, and the Levinthal paradox in the protein folding problem. Birkhauser. 1994; Ch14:491-4.

Tanihara et al., Cloning of five human cadherins clarifies characteristic features of cadherin extracellular domain and provides further evidence for two structurally different types of cadherin. Cell Adhes Commun. Apr. 1994;2(1):15-26.

Trollmo et al., Expression of the mucosal lymphocyte integrin alpha E beta 7 and its ligand E-cadherin in the synovium of patients with rheumatoid arthritis. Scand J Immunol. Sep. 1996;44(3):293-8.

Valencia et al., Cadherin-11 mediates adhesion of type B synoviocytes in rheumatoid arthritis. Arthritis & Rheumatism. Sep. 1999;42(9): S89. Abstract 111.

Van Noort et al., Cell biology of autoimmune diseases. Int Rev Cytol. 1998;178:127-206.

Breedveld, F.C, "Early Rheumatoid Arthritis. Future Treatment", *Baillière's Clinical Rheumatology*, vol. 11, 1997, pp. 83-96.

Chitaev et al., "Molecular Organization of the Desmoglein-Plakoglobin Complex", *J Cell Sci.*, Jul. 30, 1998;111 (Pt 14):1941-9.

Finck et al., Treatment of Murine Lupus with CTLA4Ig, 1:Science, Aug. 26, 1994;265(5176):1225-7.

Gorczynski et al., "An Immunoadhesin Incorporating the Molecule OX-2 Is a Potent Immunosuppressant That Prolongs Allo- and Xenograft Survival", *The American Association of Immunologists*, 1999, pp. 1654-1660.

Gorczynski et al., "CD200 Immunoadhesin Supresses Collagen-Induced Arthritis in Mice", *Clinical Immunology*, vol. 101, No. 3, December, pp. 328-334, 2001.

Noë et al., "Inhibition of adhesion and induction of epithelial cell invasion by HAV-containing E-cadherin-specific peptides", *J Cell Sci*. Jan. 1999;112 ( Pt 1):127-35.

Okazaki et al., "Molecular Cloning and Characterization of OB-cadherin , a New Member of Cadherin Family Expressed in Osteoblasts", *The Journal of Biological Chemistry*, vol. 269, No. 16, Apr. 22, 1994, pp. 12092-12098.

Steurer et al., "Ex Vivo Coating of Islet Cell Allografts with Murine CTLA4/Fc Promotes Graft Tolerance", *The American Association of Immunologists*, 1995, pp. 1165-1174.

Suzuki et al., "Diversity of the cadherin family: evidence for eight new cadherins in nervous tissue", *Cell Regulation*, vol. 2, 261-270, Apr. 1991, pp. 261-270.

Wilby et al., "N-Cadherin inhibits Schwann cell migration on astrocytes", *Mol Cell Neurosci.*, Jul. 1999;14(1):66-84.

Office Action mailed Apr. 26, 2002 for U.S. Appl. No. 09/654,328.
Office Action mailed Jan. 14, 2003, for U.S. Appl. No. 09/654,328.
Office Action mailed Dec. 15, 2003, for U.S. Appl. No. 09/654,328.
Office Action mailed Jun. 30, 2004, for U.S. Appl. No. 10/457,257.
Office Action mailed Feb. 9, 2005, for U.S. Appl. No. 10/457,257.
Office Communications mailed Nov. 3, 2008 for U.S. Appl. No. 11/986,471 (B0801.70287US02).

* cited by examiner

METHODS AND COMPOSITIONS FOR TREATMENT OF INFLAMMATORY DISEASE USING CADHERIN-11 MODULATING AGENTS

RELATED APPLICATIONS

This application is a continuation of U.S. Non-Provisional Patent Application filed Jun. 9, 2003, entitled "METHODS AND COMPOSITIONS FOR TREATMENT OF INFLAMMATORY DISEASE USING CADHERIN-11 MODULATING AGENTS", Ser. No. 10/457,257, now issued as U.S. Pat. No. 6,964,768, which is a divisional of U.S. Non-Provisional Patent Application filed Sep. 1, 2000, entitled "METHODS AND COMPOSITIONS FOR TREATMENT OF INFLAMMATORY DISEASE USING CADHERIN-11 MODULATING AGENTS", Ser. No. 09/654,328, now issued as U.S. Pat. No. 6,787,136, which claims priority to U.S. Provisional Patent Application filed Sep. 3, 1999, entitled "METHODS AND COMPOSITIONS FOR TREATMENT OF INFLAMMATORY DISEASE USING CADHERIN-11 INHIBITORY AGENTS", Ser. No. 60/152,456, now expired, and U.S. Provisional Patent Application filed Sep. 13, 1999, entitled "METHODS AND COMPOSITIONS FOR TREATMENT OF INFLAMMATORY DISEASE USING CADHERIN-11 INHIBITORY AGENTS", Ser. No. 60/153,490, now expired, the entire contents of all of which are incorporated herein by reference.

GOVERNMENT SUPPORT

This invention was made in part with government support under grant number AR34662 from the National Institutes of Health. The Government has certain rights in the invention.

FIELD OF THE INVENTION

This invention relates to methods and compositions for the treatment of inflammatory joint disorders, such as those involving synovial hyperplasia and overproduction of biologically active factors. The methods involve administering a cadherin-11 modulating agent to a subject to modulate cadherin-11 function in areas of joint damage. Screening assays for the identification of cadherin-11 modulating agents are also provided.

BACKGROUND OF THE INVENTION

The adhesive interactions between cells and between cells and the extracellular matrix are believed to play critical roles in a wide variety of processes including, for example, modulation of the immune system, regulation of developmental processes and tumor progression and metastasis. These interactions are mediated by adhesion molecules which transduce information from the extracellular to the intracellular matrix.

Four families of adhesion molecules which mediate these interactions have been identified: the integrins, the cadherins, the selecting, and immunoglobulin-related molecules. In general, adhesion molecules are transmembrane proteins which contain an extracellular domain for interacting with an extracellular matrix or cellular component, a transmembrane domain spanning the cell membrane and a cytoplasmic domain for interacting with one or more cytoskeletal or cytoplasmic components.

The cadherins play an important role in the establishment and maintenance of intercellular connections between cells of the same type (reviewed in Geiger B. et al. (1992) Annual Review of Cell Biology 8:307; Kemler R. (1993) Trends in Gastroenterology 9:317; Takeichi M. (1990) Annual Review of Biochem. 59:237; Takeichi M. (1991) Science 251:1451). Cadherins are a superfamily of structurally related molecules that function in $Ca^{+2}$-dependent homophilic adhesion. Cadherins are expressed on cells that form solid tissues, and are responsible for segregating and sorting cells during embryogenesis, establishing cell polarity, and maintaining tissue morphology. Structurally, cadherins are single chain polypeptides that are synthesized as precursors and cleaved during post-translational processing. They have large extracellular regions made up of 5 homologous domains, a single transmembrane segment and a cytoplasmic tail.

The cadherins are synthesized as precursors that are cleaved during post-translational processing. The mature cadherins are single chain molecules which include a relatively large extracellular domain (typically divided into five sections or "ectodomains"), a single transmembrane region and a cytoplasmic tail. Among the classical cadherins (i.e., P-(placenta), E-(epithelial), and N-(neural) cadherin), the cytoplasmic domain contains the highest degree of homology. The high degree of homology observed for the cytoplasmic domain reportedly is a reflection of the association of cadherins with a group of intracellular proteins, called catenins, that stabilize cadherin active conformation (Kemler R. (1993) Trends in Gastroenterology 9:317). It is generally believed that sequences in the extracellular domain are necessary to mediate homophilic (i.e., cadherin-to-cadherin) binding. A review of the literature indicates that research directed to understanding cadherin-mediated adhesion has focussed on efforts to elucidate the mechanism underlying cadherin-mediated homophilic cell adhesion. Little attention has been directed to understanding what, if any, role is played by cadherins in heterophilic adhesion. While it has been known for some time that integrins and other adhesion molecules function in immune system modulation, e.g., by playing a role in the adhesion of peripheral lymphocytes to endothelium and in homing to lymph nodes, relatively little is known regarding the mechanism by which lymphocytes home and transmigrate through the vascular endothelium to specifically target certain tissue locations, such as the synovium.

The most highly conserved sequence shared by cadherins lies within the cytoplasmic domain. It is this region that mediates interaction with the cytoplasmic catenins proteins (Hirano S. et al. Cell 70:293-301, 1992). The presence of the cytoplasmic domain is essential to functioning of the cadherin as deletions in this region abolish catenin binding as well as cell-to-cell adhesion (Hulsken J, et al. J Cell Biol 127:1375-80, 1994). The catenins ($\alpha$, 102 kDa; $\beta$, 88-93 kDa, and $\gamma$, 80-83 kDa) begin to associate with cadherins almost immediately upon biosynthesis in a stable manner that is not disrupted in TX-100 detergent (Takeichi M. Curr Opin Cell Biol 7:619-27, 1995) and are thought to mediate anchorage of cadherins to the cytoskeleton (Yap A S. et al. Annu Rev Cell Dev Biol 13:11946, 1997). Functionally, $\alpha$-catenin is necessary for cadherin mediated homophilic adhesion. Tumor cells expressing E-cadherin at the cell surface, but lacking $\alpha$-catenin expression, fail to form cell-to-cell contacts unless $\alpha$-catenin expression is restored through transfection (Chen H. et al. J Cell Sci 1141345-56, 1997; and Knudsen K A. et al. J Cell Biol 130:67-77, 1995). $\beta$-catenin is homologous to the *Drosophila* segment polarity protein armadillo as well as the cadherin associated protein plakoglobin. Plakoglobin, also termed $\gamma$-catenin, interacts more weakly with the cadherin/catenin complex, and is not always seen in cadherin precipitates.

A number of newly identified cadherin cDNA clones have been isolated using consensus oligonucleotides corresponding to cytoplasmic domain sequences that are highly conserved among cadherins and PCR cloning (Suzuki S. et al. Cell Reg 2:261-70, 1991).

Although cadherin function classically involves homophilic cell-to-cell adhesion (i.e., E-cadherin binds E-cadherin typically on another cell of the same type), however, murine E-cadherin expressed on epidermal keratinocytes also mediates adhesion to E-cadherin of Langerhans cells (Tang A. et al. Nature 361:82-5, 1993). Recently, we identified another counter-receptor for E-cadherin, namely the integrin $\alpha^E\beta_7$ which is expressed on intraepithelial T cells (Cepek K L. et al. Nature 372: 190-3, 1994 and U.S. Pat. No. 5,610,281). This represents an example of heterophilic binding of E-cadherin to the $\alpha^E\beta_7$ integrin counter-receptor.

Rheumatoid arthritis (RA) is a chronic systemic autoimmune disease of unknown etiology that affects 1-2% of the population. It is dominated by progressive joint destruction that can result in marked disability. Histologically, the joints reveal synovial hyperplasia mainly of type A synoviocytes but also of type B synoviocytes, lymphocellular infiltration of T and B cells, and neovascularization. These processes lead to the secretion of destructive factors and invasive growth of the synovial membrane (pannus) into the adjacent cartilage and bone with the consequent destruction of the joint.

SUMMARY OF THE INVENTION

The invention is based, in part, on the discovery of cadherin-11 mRNA and protein expression in cells, namely human type B synoviocytes, recovered from the synovium of patients with inflammatory joint disorders. Prior to the present discovery, cadherin-11 expression had not been reported in the synovium. Although not intending to be bound by any particular theory, it is postulated that cadherin-11 expression in cells of the synovium is involved in the homing, retention and activation of cells (such as T and B cells) in this area. In addition, cadherin-11 mediated adhesion is also postulated to mediate invasion of synovium into cartilage and bone during some inflammatory joint disorders. Synoviocyte-synoviocyte contact may also be involved in some of these disorders. Cadherin-11 mediated adhesion can be characterized as homophilic (cadherin-11 binding to cadherin-11) or heterophilic (cadherin-11 binding to a counter-receptor which is not cadherin-11). Accordingly, some of the compositions and methods of the present invention are directed towards inhibiting cadherin-11 mediated adhesion occurring between these and other cell types. Still other methods and compositions provided by the invention involve modulation of cellular functions which are mediated by cadherin-11, such as, for example, cell signaling, proliferation, apoptosis and factor secretion.

According to one aspect on the invention, a method is provided for treating a subject having an inflammatory joint disorder. The method involves administering to a subject in need of such treatment a therapeutically effective amount of a cadherin-11 modulating agent. A cadherin-11 modulating agent is an agent that modulates (e.g., enhances, inhibits, changes, etc.) a cadherin-11 function. In one particular embodiment, the cadherin-11 modulating agent is a cadherin-11 inhibitory agent. A cadherin-11 inhibitory agent is an agent which inhibits the binding of cadherin-11 to a cadherin-11 counter-receptor. In preferred embodiments, the subject is a human. In more preferred embodiments, the subject does not have abnormal cadherin-11 mediated adhesion occurring in the liver or the brain. Cadherin-11 mediated adhesion is the binding of cadherin-11 to its counter-receptor.

In one embodiment, the inflammatory joint disorder is chronic synovitis. In another embodiment, the inflammatory joint disorder is an autoimmune disease. In a preferred embodiment, the autoimmune disease is rheumatoid arthritis.

The cadherin-11 inhibitory agent may be administered systemically. In preferred embodiments, the cadherin-11 inhibitory agent is administered locally to a synovium or the synovial fluid of a subject.

The cadherin-11 inhibitory agent can inhibit cadherin-11 binding to a cadherin-11 counter-receptor in a number of ways. In one embodiment, the cadherin-11 inhibitory agent binds selectively to cadherin-11. In another embodiment, the cadherin-11 inhibitory agent binds selectively to a cadherin-11 counter-receptor. Exemplary inhibitory agents are described in the detailed description. In all of these embodiments, the cadherin-11 inhibitory agent functions to inhibit cadherin-11 mediated adhesion.

The cadherin-11 and the cadherin-11 counter-receptor may be expressed by the same or different cell types. The cadherin-11 counter-receptor need not be on a cell surface but rather may be part of an interstitial material or it may be a secreted material that binds to any other molecule or surface. As an example of the latter embodiment, the cadherin-11 counter-receptor is a component of an extracellular matrix of a tissue, a cartilage or a bone. The cadherin-11 counter-receptor may also be a molecule secreted by a cell. In certain embodiments, cadherin-11 is expressed by one cell and the cadherin-11 counter-receptor is expressed by another, distinct cell. Cadherin-11 expressing cells may be selected from the group consisting of a type A or a type B synoviocyte, a synovial derived fibroblast, a synovial membrane lining cell, an osteoblast, a cartilage-derived cell and an invasive pannus-derived cell. Cadherin-11 counter-receptor expressing cells may be selected from the group consisting of a T lymphocyte, a B lymphocyte, a plasma cell, a macrophage, a dendritic cell, a natural killer (NK) cell, a mast cell, a type A or a type B synoviocyte, a synovial derived fibroblast, an osteoblast, a cartilage-derived cell, a synovial membrane lining cell and an invasive pannus-derived cell.

In some embodiments, the cadherin-11 modulating agents, such as for example, the cadherin-11 inhibitory agents are not antibodies, such as for example monoclonal antibodies. In some embodiments, the agents of the invention do not include the antibodies disclosed in U.S. Pat. No. 5,597,725 and in PCT application PCT/US93/03681 (WO/93/21302). Thus, in certain related embodiments, the agents of the invention do not embrace the monoclonal antibodies produced by the hybridomas designated 30Q8A (HB11316), 30Q4H (HB11317), 45A5G (HB 11318), 30S2F (HB11319), 45C6A (HB11320), 30T11G (HB11324), 64G11F (HB 11527).

The invention provides in another aspect a method for screening a molecular library to identify an agent (e.g., a pharmaceutical lead compound) that modulates cadherin-11 mediated adhesion between a first cell that expresses cadherin-11 and a second cell that expresses a cadherin-11 counter-receptor. The agent may inhibit the cadherin-11 mediated adhesion, in which case, it is a cadherin-11 inhibitory agent. The method involves performing a first adhesion assay between the first cell and the second cell to obtain a first adhesion assay result, performing a second adhesion assay between the first cell and the second cell in the presence of at least one molecular library member to obtain a second adhesion assay result, and comparing the first and the second adhesion assay results to determine whether the at least one molecular library member modulates cadherin-11 mediated adhesion between the first cell and the second cell. The cell types, cadherin molecules and inhibitory agents are as described above and in the detailed description.

According to one embodiment, the first cell is selected from the group consisting of a synoviocyte such as a type A synoviocyte, a type B synoviocyte, a synovial derived fibroblast, a synovial membrane lining cell and an osteoblast. The second cell may be selected from the group consisting of a type A synoviocyte, a type B synoviocyte, a synovial derived fibroblast, a synovial membrane lining cell, an osteoblast, a T lymphocyte, a B lymphocyte, a plasma cell, a macrophage, a dendritic cell, a natural killer cell and a mast cell. In yet another embodiment, the first cell is derived from the invasive pannus and the second cell is derived from cartilage. In a further embodiment, the first cell is derived from the invasive pannus and the second cell is an osteoblast.

According to the screening method provided, a difference in the first and the second adhesion assay results is indicative of the presence of at least one molecular library member that modulates cadherin-11 mediated adhesion between the first cell and the second cell. The assay can be designed to identify agents which inhibit or enhance the cadherin-11 mediated adhesion.

The molecular library may be recombinantly produced or chemically synthesized. In still other embodiments, the molecular library is a peptide library.

In yet another aspect of the invention, another method for screening a molecular library to identify a pharmaceutical lead compound that modulates cadherin-11 mediated adhesion is provided. The method involves performing a first adhesion assay between cadherin-11 and a cadherin-11 counter-receptor to obtain a first adhesion assay result, performing a second adhesion assay between cadherin-11 and the cadherin-11 counter-receptor in the presence of at least one molecular library member to obtain a second adhesion assay result, and comparing the first and the second adhesion assay results to determine whether the at least one molecular library member modulates cadherin-11 mediated adhesion.

In certain embodiments of the invention, the cadherin-11 counter-receptor is selected from the group consisting of a cadherin, an integrin, an integrin subunit, an immunoglobulin family member and a carbohydrate. In preferred embodiments, the cadherin is cadherin-11. In one embodiment, the cadherin-11 counter-receptor is a cadherin-11 fusion polypeptide. In still another embodiment, the cadherin-11 counter-receptor is an antibody that binds selectively to cadherin-11.

The cadherin-11 and/or the cadherin-11 counter-receptor may be isolated. The cadherin-11 and/or the cadherin-11 counter-receptor may also be soluble.

In yet another embodiment, cadherin-11 is presented by a cell. In yet a further embodiment, the cadherin-11 counter-receptor is presented by a cell. The cell expressing cadherin-11 may be selected from the group consisting of a type A or a type B synoviocyte, a synovial derived fibroblast, a synovial membrane lining cell, an osteoblast, a cartilage-derived cell and an invasive pannus-derived cell. The cell expressing cadherin-11 counter-receptor may be selected from the group consisting of a synoviocyte, a synovial derived fibroblast, a synovial membrane lining cell, an osteoblast, a cartilage-derived cell, an invasive pannus-derived cell, a T lymphocyte, a B lymphocyte, a plasma cell, a macrophage, a dendritic cell, a mast cell and a natural killer cell. In still other embodiments, the cadherin-11 counter-receptor may be a component of an extracellular matrix of tissue, cartilage or bone, or it may be a molecule secreted by a cell and found anywhere in a tissue.

In another aspect, the invention provides a method for treating a subject having an inflammatory joint disorder comprising administering to a subject in need of such treatment a therapeutically effective amount of an agent which modulates a cellular function in a cadherin-11 expressing cell, preferably a cellular function other than cadherin-11 mediated adhesion. The agent may modulate the activity by interacting directly with cadherin-11 (e.g., a binding agent which selectively binds to cadherin-11 and thereby modulates its activity) or indirectly by interacting with another cellular component which then modulates the cadherin-11 activity. The cellular function may be selected from the group consisting of cell proliferation, factor secretion, apoptosis, migration, and/or attachment. In important embodiments, the agent which modulates a cellular function in a cadherin-11 expressing cell does not inhibit binding of cadherin-11 to a cadherin-11 counter-receptor. Thus, in some embodiments, the cellular function is not cadherin-11 binding to a cadherin-11 counter-receptor (i.e., the cellular function is not cadherin-11 mediated adhesion).

In yet another aspect of the invention, a method for screening a molecular library to identify a pharmaceutical lead compound that modulates a cellular function in a cadherin-11 expressing cell (preferably, a cellular function other than cadherin-11 mediated adhesion) is provided. The method comprises determining a first value of the cellular function for a cadherin-11 expressing cell in the absence of a molecular library member, determining a second value of the cellular function for a cadherin-11 expressing cell in the presence of at least one molecular library member, and comparing the first value and the second value to determine whether the at least one molecular library member modulates a cellular function in a cadherin-11 expressing cell. The cellular function may be selected from the group consisting of cell proliferation, factor secretion, apoptosis, migration and/or attachment.

In a related aspect, the invention provides a similar method for screening a molecular library to identify a pharmaceutical lead compound that modulates factor secretion in a cadherin-11 expressing cell. In one embodiment of this latter aspect, the factor secretion is selected from the group consisting of the factor secretion is selected from the group consisting of stromelysin secretion, collagen secretion, collagenase secretion and IL-6 secretion.

In a similar manner, the screening method can be used to identify pharmaceutical lead compounds that modulate a cellular function in a cadherin-11 counter receptor expressing cell. In important embodiments, the pharmaceutical lead compound is screened for its ability to inhibit cadherin-11 binding to a cadherin-11 counter-receptor. Preferably, in certain embodiments, the pharmaceutical lead compound does not inhibit binding of cadherin-11 to its counter-receptor. Thus in some embodiments, the cellular function which is modulated is not cadherin-11 binding to a cadherin-11 counter-receptor.

The invention also provides, in another aspect, a pharmaceutical composition (i.e., a pharmaceutical preparation) comprising an effective amount of a cadherin-11 modulating agent (e.g., a cadherin-11 inhibitory agent) and a pharmaceutically acceptable carrier as well as a method for making such a composition. The cadherin-11 modulating agent is present in an amount effective to modulate cadherin-11 function. If the agent is a cadherin-11 inhibitory agent, then it may be present in an amount effective to inhibit cadherin-11 mediated adhesion (such as, for example, that which occurs in the synovium). In one embodiment, the composition is contained in a syringe for injection locally to the synovium, synovial fluid, joint or joint capsule of a subject.

The invention further provides a method of making a pharmaceutical composition, a pharmaceutical preparation and/or a medicament, i.e., by placing the cadherin-11 modulating agent (e.g., a cadherin-11 inhibitory agent) of the invention in a pharmaceutically acceptable carrier. The pharmaceutical composition preparation may contain one or more cadherin-11 modulating agents and, optionally, other therapeutic agents which are useful in the treatment of disorder described herein (e.g., NSAIDs).

These and other aspects of the invention, as well as various advantages and utilities, will be more apparent with reference to the detailed description of the preferred embodiments and to the accompanying drawings.

BRIEF DESCRIPTION OF THE DRAWINGS

The Examples refer to and include a brief description of various figures. It is to be understood that the drawings or figures are illustrative only and are not required for the enablement of the inventions disclosed herein.

Sequence Listing

Figure 1:
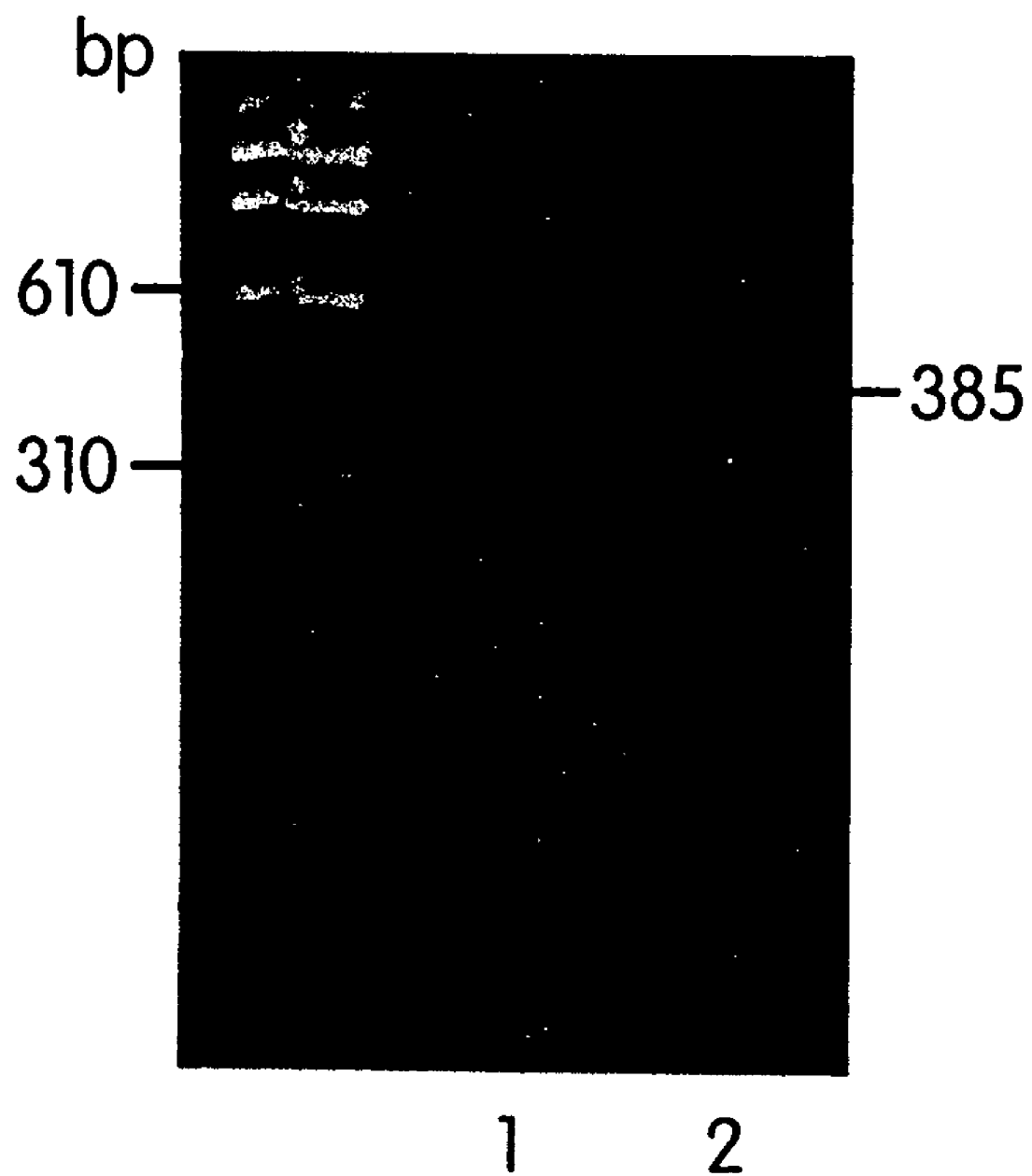
FIG. 1 illustrates gel electrophoresis separated PCR products. The negative control is shown in lane 1 and the expected 385 bp size product obtained in type B synoviocytes cDNA is shown in lane 2.

SEQ ID NO: 1 is the nucleotide sequence of human cadherin-11 cDNA.

SEQ ID NO: 2 is the amino acid sequence of human cadherin-11 protein.

SEQ ID NO: 3 is the amino acid sequence of human E-cadherin residues 753-762.

SEQ ID NO: 4 is the amino acid sequence of human E-cadherin residues 840-847.

SEQ ID NO: 5 is the amino acid sequence of human E-cadherin residues 853-859.

SEQ ID NO: 6 is the amino acid sequence of human E-cadherin residues 865-875.

SEQ ID NO: 7 is the nucleotide sequence of a degenerate sense primer.

SEQ ID NO: 8 is the nucleotide sequence of a degenerate antisense primer.

SEQ ID NO: 9 is the nucleotide sequence of primer XV14.

SEQ ID NO: 10 is the nucleotide sequence of primer XV15.

SEQ ID NO: 11 is the nucleotide sequence of primer XVCad11A.

SEQ ID NO: 12 is the nucleotide sequence of primer XVCad11E.

DETAILED DESCRIPTION OF THE INVENTION

The invention is premised, in part, on the discovery that cadherin-11 mRNA and protein are expressed in cells of the synovium of patients with inflammatory joint disorders. The discovery was made by co-precipitating cadherin-11 with an antiserum to catenin in type B human synoviocytes. The demonstration of expression of a cadherin, namely cadherin-11, in the synovium of a rheumatoid arthritis patient provides a previously unrecognized opportunity to target therapies at ameliorating rheumatoid arthritis as well as other inflammatory arthritis in which synovial hyperplasia and overproduction of toxic and biologically active factors mediate joint damage.

Cadherin-11 is a transmembrane molecule that, inter alia, mediates binding of cells to each other through interaction with itself or its counter-receptors. Like other cadherins, cadherin-11 is proposed to mediate adhesion of like cells to each other as well as adhesion of cells of different lineages to each other. According to the discovery upon which the present invention is based, cadherin-11 is proposed, inter alia, to mediate adhesion between like cells such as synoviocytes as well as different cells such as synoviocytes and lymphocytes (e.g., T and B cells).

The human and mouse cadherin-11 genes have been isolated and sequenced previously (Suzuki S. et al. Cell Reg 2:261-70, 1991). See also, Genbank Accession No. NM_001797, (SEQ ID NO: 1 and SEQ ID NO: 2) for the human cadherin-11 cDNA and predicted amino acid sequences, respectively.

Lymphocytes have the ability to circulate through blood vessels and then either sample antigens or provide immune protection in all tissues. Specific adhesion molecules (e.g., selectins and integrins) and their counter-receptors are believed to mediate lymphocyte homing and transmigration through the vascular endothelium at sites of inflammation (Springer T A. Cell 76:301-314, 1994). Each integrin is a noncovalently associated αβ heterodimeric complex. Integrin subfamilies have been defined by the use of particular β chains which often pair with one of several different a chains. Only selected integrins are expressed on T cells. Members of the $\beta_1$ and $\beta_3$ subfamily ($\alpha^1\beta_1, \alpha^2\beta_1, \alpha^4\beta_1\, \alpha^5\beta_1$ and $\alpha^v\beta_3$) are primarily involved in lymphocyte adhesion to extracellular matrix, except for the $\alpha^4\beta_1$, heterodimer (VLA-4) that binds to vascular cell adhesion molecule-1 (VCAM-1), a counter-receptor on activated vascular endothelium (Elices M J. et al. Cell 60:577-584, 1990). Of the α subfamily, LFA-1 ($\alpha^L\beta_2$) is expressed on T cells and mediates binding to counter-receptors ICAM-1 (Marlin S D. et al. Cell 51:813-819, 1987), ICAM-2 (deFourgerolles A R. et al. J Exp Med 174:253-267, 1991) and ICAM-3 (deFourgerolles A R. et al. J Exp Med 175:185-190, 1992; Fawcett J. et al. Nature 360:481-484, 1992; and Vazeux R. et al. Nature 1992;360:481-488). LFA-1 also mediates attachment to inflamed vascular endothelium allowing firm attachment of T lymphocytes prior to their transmigration out of the blood-stream. The migration of lymphocytes into inflammatory sites involves a multi-step process in which selectins (such as L-selectin on T-cells) mediate rolling, following which integrin activation results in LFA-1 and VLA-4 mediated tight attachment, followed by transmigration into tissues. This trafficking of lymphocytes is a requirement for lymphocyte accumulation at sites of infection, or abnormally at sites of chronic inflammation such as rheumatoid synovium.

Thus, the invention embraces the use of cadherin-11 modulating agents in the treatment of inflammatory joint disorders. Additionally, screening methods are provided for the identification of cadherin-11 modulating agents which possess the characteristics described herein.

The methods and compositions of the invention relate to cadherin-11 modulating agents. A cadherin-11 modulating agent, as used herein, embraces agents which inhibit the binding of cadherin-11 to its counter-receptor (i.e., cadherin-11 inhibitory agents) and agents which modulate cellular functions in cadherin-11 expressing cells (e.g., agents which trigger, or those which inhibit, cadherin-11 associated signaling). Cadherin-11 modulating agents are able to modulate (1) cell proliferation, (2) secretion of molecules such as, but not limited to, stromelysin, collagen, collagenase and IL-6, (3) apoptosis, (4) migration and/or (5) attachment, of cadherin-11 expressing cells. In important embodiments, such agents lead to a decrease in cell proliferation, a decrease in the secretion of molecules such as, but not limited to, cytokines, and an increase in apoptosis in cells expressing cadherin-11. In effect, these agents preferably function to slow the rate of growth of, or ultimately kill, cadherin-11 cells such as synoviocytes. It has been reported previously in other cell types that loss of E-cadherin may lead to a cancerous or metastatic phenotype.

The invention thus also embraces cadherin-11 inhibitory agents and their method of use. Unless otherwise stated, it is to be understood that these two categories of agents, i.e., agents which modulate cadherin-11 mediated adhesion (i.e., cadherin-11 inhibitory agents) and agents which modulate other cadherin-11 functions, such as proliferation, factor secretion, and apoptosis, need not be mutually exclusive nor need they be completely overlapping. For example, it is expected that some agents identified in the screening assays of the invention will function solely as cadherin-11 inhibitory agents (i.e., having the ability to block cadherin-11 binding to its counter-receptor), others will function by modulating (e.g., enhancing or inhibiting) cellular functions, such as proliferation, secretion, apoptosis, attachment and migration, while still other agents will be capable of both. Thus, some agents will be capable of inhibiting cadherin-11 binding to its counter-receptor, yet have no impact upon other cadherin-11 mediated functions such as cell signaling. Similarly, other agents will enhance or inhibit cadherin-11 mediated functions such as proliferation, for example, yet have no effect on cadherin-11 binding to its counter-receptor.

In one aspect, the invention is directed to a method for treating a subject having an inflammatory joint disorder. As used herein, an inflammatory joint disorder is one in which synovial hyperplasia and/or overproduction of biologically active factors mediate joint damage. In inflammatory joint disorders, the synovium becomes inflamed and thickened, and in advanced cases, this is followed by an invasion of the synovium into the cartilage and bone. The synovium is the membrane lining the capsule of a joint. Synovitis (i.e., inflammation of the synovium) can be manifest in either acute or chronic forms. In acute synovitis, the onset of pain and discomfort is usually sudden and of short duration, as is also the case in pigment villonodular synovitis. In contrast, in chronic synovitis, the pain and discomfort are recurrent and persistent. In either case, the symptoms can be brought on by arthritis, injury, overuse of the joint and infection.

The modulating agent, such as the inhibitory agent, is preferably administered locally to the synovium of the subject. Affected joints which can be treated are those which exist throughout the body, in areas such as the shoulders, back, wrists, hands, elbows, knees, hips, ankles and feet, and are lined by a synovial membrane.

Exemplary conditions that result from or cause inflammatory joint disorders include chronic synovitis, autoimmune disorders, psoriatic arthritis, chronic Lyme disease arthritis, arthritis associated with inflammatory bowel disease, arthritis associated with ankylosing spondylitis, Reiter's syndrome, arthritis associated with systemic lupus erythrematosus, arthritis associated with juvenile chronic arthritis, arthritis associated with infection, arthritis associated with immune response to infectious agents and nonspecific synovitis of unknown etiology. An autoimmune disorder is one in which the body's immune system reacts against one or more body tissues and thus attacks the tissue as it would a foreign antigen or pathogen. Rheumatoid arthritis is an example of an autoimmune disorder in which the immune system components perpetuate inflammation of a joint, resulting in damage to the synovium, cartilage, bone, and associated joint tissues.

One method provided by the invention involves administering to a subject in need of such treatment a cadherin-11 inhibitory agent. A cadherin-11 inhibitory agent is an agent which inhibits the binding of cadherin-11 to a cadherin-11 counter-receptor. The cadherin-11 inhibitory agent is administered to the subject in a therapeutically effective amount. A therapeutically effective amount is a dosage of the cadherin-11 inhibitory agent sufficient to provide a medically desirable result. In the treatment method of the invention, the therapeutically effective amount of the cadherin-11 inhibitory agent may be that amount which is sufficient to reduce the inflammation or swelling of the joint, or to alleviate the pain at the joint. As used herein, treatment embraces the use of the cadherin-11 inhibitory agents in reducing the adverse medical condition that is mediated by cadherin-11 binding to its counter-receptor in vivo, as well as prophylactic treatment of subjects at risk of developing an inflammatory joint disorder.

As mentioned earlier, the treatment methods described herein embrace the use of either or both cadherin-11 inhibitory agents and agents which modulate cellular functions (e.g., signaling, proliferation, apoptosis, etc.) of cadherin-11 other than cadherin-11 binding to a cadherin-11 counter-receptor. Thus, as described herein, the method of treatment of a subject having an inflammatory joint disorder may alternatively comprise administering to the subject an effective amount of an agent that modulates one or more cellular functions of cadherin-11. In important embodiments, the one or more cellular functions do not include cadherin-11 binding to its counter-receptor.

A subject, as used herein, refers to any mammal susceptible to having or presently having an inflammatory joint disorder. Preferably, the subject is one having an inflammatory joint disorder. In more preferred embodiments, the subject is a human. In certain embodiments, the subject does not have abnormal cadherin-11 mediated adhesion in the brain and/or liver.

In general, cadherin-11 inhibitory agents are agents which inhibit cadherin-11 mediated adhesion. Cadherin-11 mediated adhesion, as used herein, refers to the binding of a cadherin-11 polypeptide, herein after referred to as cadherin-11, to a cadherin-11 counter-receptor. A cadherin-11 counter-receptor is a molecule which selectively binds to cadherin-11 and, in some instances, is expressed at the surface of a cell. In other instances, the cadherin-11 counter-receptor is not cell-bound but is rather a component of an interstitial matrix such as an extracellular matrix of tissue, cartilage or bone. The cadherin-11 counter-receptor may also be a molecule secreted by a cell. Exemplary cells which express a cadherin-11 counter-receptor include type A and type B synoviocytes, synovial-derived fibroblasts, cartilage-derived cells, osteoblasts, T and B lymphocytes, plasma cells, macrophages, dendritic cells, NK cells, mast cells, synovial lining cells, and cells derived from the invasive pannus. A cadherin-11 counter-receptor embraces cadherin-11, members of the immunoglobulin superfamily, carbohydrate epitopes of a glycoprotein or glycolipid, a selectin, a lectin containing ligand and an integrin. At least 21 different integrins have been identified composed from eight different $\beta$ chains associated with 15 different $\alpha$ chains. Integrins useful in the invention include $\alpha^1\beta_1$, $\alpha^2\beta_1$, $\alpha^3\beta_1$, $\alpha^4\beta_1$, $\alpha^5\beta_1$, $\alpha^6\beta_1$, $\alpha^7\beta_1$, $\alpha^8\beta_1$, $\alpha^9\beta_1$, $\alpha^1\beta_2$, $\alpha^M\beta_2$, $\alpha^x\beta_2$, $\alpha^{IIb}\beta_3$, $\alpha^v\beta_3$, $\alpha^6\beta_4$, $\alpha^v\beta_5$, $\alpha^4\beta_7$, $\alpha^E\beta_7$, $\alpha^6\beta_7$. In some embodiments, the preferred integrins are $\alpha^1\beta_1$, $\alpha^2\beta_1$, $\alpha^3\beta_1$, $\alpha^4\beta_1$, $\alpha^5\beta_1$, $\alpha^6\beta_1$, $\alpha^L\beta_2$, $\alpha^M\beta_2$, $\alpha^v\beta_3$, $\alpha^4\beta_7$ and $\alpha^E\beta_7$.

The invention is premised in part on the observation that T cells and B cells, both of which have not been previously reported to express cadherin-11, are capable of binding to immobilized recombinant cadherin-11 in vitro. Thus, this finding suggests that T and B cells express a cadherin-11 counter-receptor which is not cadherin-11. This is the first report of a cadherin-11 counter-receptor which is not cadherin-11 expressed by T and B cells. By comparing cells which bind to purified or isolated cadherin-11 (and which are known not to express cadherin-11) to cells which are incapable of such binding, cadherin-11 counter-receptors which are not cadherin-11 can be identified. Exemplary methods for comparison of these two cell types include, e.g., genetic screening using techniques such as differential display, as well as, subtractive hybridization to identify transcripts which are expressed by the cadherin-11 binding cells and not expressed by the cadherin-11 non-binding cells. These techniques are routinely practiced by those of ordinary skill in the art. These techniques allow for the rapid isolation of nucleic acid coding for a cadherin-11 counter-receptor. Once cells have been identified which bind cadherin-11 but do not express cadherin-11 are identified, cellular membrane preparations can be analyzed by, for example, affinity purification to isolate the cadherin-11 counter-receptor. For example, a GST-cadherin-11 fusion protein immobilized on a column can be used to extract cadherin-11 counter-receptors from a crude cell preparation. In a preferred embodiment, monoclonal antibodies are generated against cells that express a cadherin-11 counter-receptor and the resultant antibodies are screened for their ability to block cadherin-11 binding to such cells.

The cadherin-11 modulating agents of the invention, including the cadherin-11 inhibitory agents, embrace nucleic acid molecules, polypeptides, carbohydrates, and synthetically-produced and recombinantly-produced molecules.

In certain other embodiments of the invention, the cadherin-11 modulating agent is a polypeptide (i.e., a cadherin-11 modulating polypeptide). As such, the modulating agent, including the cadherin-11 inhibitory agent, may be (1) a cadherin-11 polypeptide or a fragment (preferably unique) thereof, or (2) a cadherin-11 counter-receptor polypeptide or a fragment (preferably unique) thereof; (3) a cadherin-11 "binding peptide" (other than a cadherin-11 counter-receptor); and (4) a cadherin-11 counter-receptor "binding peptide" (other than a cadherin-11 polypeptide). As used herein, a cadherin-11 binding peptide refers to peptides which bind selectively to cadherin-11. Similarly, a cadherin-11 counter-receptor binding peptide refers to a peptide which binds selectively to cadherin-11 counter-receptor. In some important embodiments, the cadherin-11 binding peptide does not inhibit the binding of cadherin-11 to a cadherin-11 counter-receptor. That is to say, that in certain embodiments, the binding peptide is not a cadherin-11 inhibitory agent, but it may still modulate other cadherin-11 mediated functions such as proliferation. The same may be true for cadherin-11 counter-receptor binding peptides. The invention embraces the use of these latter two classes of binding peptides in the treatment of subjects where it is not necessary to inhibit cadherin-11 binding to a cadherin-11 counter-receptor in order to effect treatment.

Binding peptides can be antibodies or fragments of antibodies ("binding polypeptides"), having the ability to bind selectively to cadherin-11 or cadherin-11 counter-receptor polypeptides. Antibodies include polyclonal and monoclonal antibodies which can be prepared according to conventional methodology. Binding peptides and binding polypeptides can also be derived from sources other than antibody technology. For example, such binding peptides can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties. Exemplary cadherin-11 binding peptides which are antibodies and fusion proteins are described in the Examples. (See also, U.S. Pat. Nos. 5,639,634 and 5,597,725 and PCT Patent Application No. WO93/21302, the entire contents of which are incorporated by reference herein.)

Cadherin-11 inhibitory polypeptides may be cell adhesion molecules such as integrins and cadherins.

Cadherin-11 inhibitory polypeptides are useful for inhibiting the binding of cadherin-11 to its counter-receptor. As used herein, a fragment of a polypeptide refers to one which is capable of binding to either cadherin-11 or the cadherin-11 counter-receptor, as the case may be. The preferred cadherin-11 inhibitory polypeptides of the invention have the amino acid sequence of SEQ. ID NO. 2 or a functionally equivalent fragment of SEQ. ID NO.2. Thus, cadherin-11 inhibitory polypeptides embrace functionally equivalent fragments, variants, and analogs of SEQ. ID NO. 2, provided that the fragments, variants, and analogs bind to cadherin-11 or to a cadherin-11 counter-receptor and, thereby, reduce or prevent cadherin-11 adhesion to its counter-receptor. The invention also embraces proteins and peptides coded for by any of the foregoing cadherin-11 inhibitory nucleic acid molecules.

A unique fragment of a cadherin-11 polypeptide, in general, has the features and characteristics of unique fragments as discussed herein in connection with nucleic acids. As will be recognized by those skilled in the art, the size of the unique fragment will depend upon factors such as whether the fragment constitutes a portion of a conserved protein domain.

Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length polypeptide). Virtually any segment of SEQ ID NO:2 that is 9 or more amino acids in length and which is not common to other distinct polypeptides will be unique. Unique fragments of a polypeptide preferably are those fragments which retain a distinct functional capability of the polypeptide. Functional capabilities which can be retained in a unique fragment of the cadherin-11 polypeptide include the ability to bind to a cadherin-11 counter-receptor. Similarly a unique fragment of a cadherin-11 counter-receptor polypeptide will possess the ability to bind to a cadherin-11 polypeptide.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

Phage display can be particularly effective in identifying binding peptides useful according to the invention. Briefly, one prepares a phage library (using e.g. m13, fl, or lambda phage), displaying inserts from 4 to about 80 amino acid residues using conventional procedures. The inserts may represent, for example, a completely degenerate or biased array. One then can select phage-bearing inserts which bind to the cadherin-11 or cadherin-11 counter-receptor polypeptide. This process can be repeated through several cycles of reselection of phage that bind to the cadherin-11 or cadherin-11 counter-receptor polypeptide. Repeated rounds lead to enrichment of phage bearing particular sequences. The displayed peptide sequence can vary in size. As the size increases, the complexity of the library increases. It is preferred that the total size of the displayed peptide sequence (the random amino acids plus any spacer amino acids) should not be greater than about 100 amino acids long, more preferably not greater than about 50 amino acids long, and most preferably not greater than about 25 amino acids long. In certain embodiments, the libraries may have at least one constraint imposed upon the displayed peptide sequence. A constraint includes, but is not limited to, a positive or negative charge, hydrophobicity, hydrophilicity, a cleavable bond and the necessary residues surrounding that bond, and combinations thereof. In certain embodiments, more than one constraint is present in each of the peptide sequences of the library.

DNA sequence analysis can be conducted to identify the sequences of the expressed polypeptides. The minimal linear portion of the sequence that binds to the cadherin-11 or cadherin-11 counter-receptor polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cadherin-11 or cadherin-11 counter-receptor polypeptides. Thus, the cadherin-11 or cadherin-11 counter-receptor polypeptides of the invention, or a fragment thereof, can be used to screen peptide libraries, including phage display libraries, to identify and select peptide binding partners of the cadherin-11 or cadherin-11 counter-receptor polypeptides of the invention. Such molecules can be used, as described, for screening assays, for purification protocols, for interfering directly with the functioning of cadherin-11 or cadherin-11 counter-receptor and for other purposes that will be apparent to those of ordinary skill in the art.

A cadherin-11 or cadherin-11 counter-receptor polypeptide, or a fragment thereof, also can be used to isolate other binding partners (e.g., naturally occurring cadherin-11 counter-receptors). Isolation of binding partners may be performed according to well-known methods. For example, isolated cadherin-11 or cadherin-11 counter-receptor polypeptides can be attached to a substrate, and then a solution suspected of containing an cadherin-11 or cadherin-11 counter-receptor binding partner may be applied to the substrate. If the binding partner for cadherin-11 or cadherin-11 counter-receptor polypeptides is present in the solution, then it will bind to the substrate-bound cadherin-11 or cadherin-11 counter-receptor polypeptide. The binding partner then may be isolated.

In some important embodiments, the cadherin-11 inhibitory agent is a functionally equivalent peptide analog of cadherin-11 or a cadherin-11 counter-receptor. As used herein, the term functionally equivalent peptide analog refers to a peptide analog that is capable of inhibiting the binding of cadherin-11 to the cadherin-11 counter-receptor by competing either with cadherin-11 for binding to a counter-receptor of cadherin-11 or with cadherin-11 counter-receptor for binding to cadherin-11. Functionally equivalent peptide analogs of cadherin-11 are identified, for example, in in vitro adhesion assays, as described below and in the Examples, that measure the ability of the peptide analog to inhibit cadherin-11-mediated adhesion either between cells expressing cadherin-11 and its counter-receptor or between isolated cadherin-11 and isolated cadherin-11 counter-receptor, or some combination thereof. Accordingly, exemplary functionally equivalent peptide analogs of cadherin-11 include the extracellular domain of cadherin-11, fragments of the extracellular domain and peptide analogs of the extracellular domain (e.g., peptides which contain conservative amino acid substitutions), provided that the peptide fragments and analogs are capable of inhibiting adhesion between cadherin-11 and its counter-receptor when these molecules are present in isolated form or in the context of a cell membrane in vivo and/or in vitro. Likewise, a functionally equivalent peptide analog of cadherin-11 counter-receptor includes the extracellular domain of cadherin-11 counter-receptor, fragments of the extracellular domain and peptide analogs of the extracellular domain (e.g., peptides which contain conservative amino acid substitutions), provided that the peptide fragments and analogs are capable of inhibiting adhesion between cadherin-11 and its counter-receptor when these molecules are present in isolated form or in the context of a cell membrane in vivo and/or in vitro. Preferably, the peptide fragments and/or analogs contain between about three and about one hundred amino acids. More preferably, the peptide analogs contain between about ten and about twenty-five amino acids.

The inhibitory agents of the invention include antibodies and fusion proteins that inhibit binding of cadherin-11 to its counter-receptor. Thus, the peptides of the invention can be specifically reactive with an antibody (preferably a monoclonal antibody) that binds selectively to cadherin-11 or an antibody that binds selectively to cadherin-11 counter-receptor and thereby inhibits adhesion between cadherin-11 and a counter-receptor of cadherin-11. Thus, fusion polypeptides of cadherin-11 and cadherin-11 counter-receptor are also embraced by the present invention, as is their use in the methods disclosed herein. A fusion polypeptide, as used herein, is a polypeptide which contains peptide regions from at least two different proteins. For example, a fusion cadherin-11 polypeptide can be formed by fusing, usually at the nucleotide level, coding sequence from cadherin-11 to coding sequence from another distinct protein. As described below, a cadherin-11 GST fusion protein can be synthesized and is useful in screening for agents which bind to cadherin-11. Also as described in the Examples, a cadherin-11-Fc fusion protein has been synthesized by joining the extracellular domains of cadherin-11 to the Fc portion of immunoglobulin. Depending on their nature, some fusion proteins are suited for in vitro use while others are better suited to in vivo use.

In certain preferred embodiments, the cadherin-11 modulating agent is an antibody or a fragment of an antibody having the ability to selectively bind to cadherin-11 or cadherin-11 counter-receptor polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

For inoculation or prophylactic uses, the antibodies of the present invention are preferably intact antibody molecules including the Fc region. Such intact antibodies will have longer half-lives than smaller fragment antibodies (e.g. Fab) and are more suitable for intravenous, intraperitoneal, intramuscular, intracavity, subcutaneous, or transdermal administration.

Fab fragments, including chimeric Fab fragments, are preferred in methods in which the peptides of the invention are administered directly to a local tissue environment. For example, the Fab fragments are preferred when the peptide of the invention is administered directly to the afflicted joint or to the inflamed synovium. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. Production of Fabs in *E. coli* makes it possible to produce these antibody fragments in large fermenters which are less expensive than cell culture-derived products.

A cadherin-11 modulating agent may also be a nucleic acid molecule (i.e., a cadherin-11 modulating nucleic acid molecule). A cadherin-11 modulating nucleic acid molecule is a nucleic acid molecule that functions to modulate a cadherin-11 cellular function, such as for example, cell proliferation, factor secretion, apoptosis, migration and attachment. A cadherin-11 inhibitory nucleic acid molecule is a nucleic acid molecule that functions to inhibit cadherin-11 mediated adhesion. These nucleic acid molecules may function directly (e.g., as antisense nucleic acid molecules) or indirectly (e.g., via the peptides and/or polypeptides they encode). A cadherin-11 modulating nucleic acid molecule and a cadherin-11 inhibitory nucleic acid molecule may be selected from a group consisting of nucleic acid molecules which (1) encode a cadherin-11 polypeptide or a fragment (preferably unique) thereof; (2) encode a cadherin-11 counter-receptor polypeptide or a fragment (preferably unique) thereof, or (3) are cadherin-11 or cadherin-11 counter-receptor antisense molecules which inhibit the transcription or translation of the foregoing nucleic acid molecules.

In one embodiment, a cadherin-11 modulating nucleic acid such as, for example, a cadherin-11 inhibitory nucleic acid, (1) hybridizes under stringent conditions to a nucleic acid having a sequence of SEQ ID NO: 1, and (2) codes for a cadherin-11 polypeptide or a fragment (preferably unique) thereof that is capable of binding specifically to cadherin-11 or a cadherin-11 counter-receptor. In one embodiment, the cadherin-11 polypeptide, or fragment thereof, binds to a cadherin-11 counter-receptor on the surface of another cell, and thereby, inhibits the binding of cadherin-11 to its counter-receptor and, optionally inhibits the binding of one cell to another. The inhibition of the binding of one cell to the extracellular matrix is also envisioned. The preferred cadherin-11 inhibitory nucleic acid molecule has a nucleotide sequence of SEQ ID NO:1. The cadherin-11 modulating nucleic acid molecules of the invention also include homologs and alleles of a nucleic acid molecule having a sequence of SEQ ID NO: 1.

The cadherin-11 modulating nucleic acid molecules, and preferably the cadherin-11 inhibitory nucleic acid molecules, may encode polypeptides which are soluble cadherin-11 polypeptides or membrane-bound polypeptides. The soluble cadherin-11 polypeptides lack a transmembrane domain and, optimally, contain further amino acids which render the polypeptide soluble (e.g., fusion proteins, containing all or part of cadherin-11, which inhibit the binding of cadherin-11 to its counter-receptor). Cadherin-11 modulating agents which are membrane-bound (or membrane associated) preferably contain a transmembrane domain.

Cadherin-11 modulating nucleic acid molecules, and preferably cadherin-11 inhibitory nucleic acid molecules, further embrace nucleic acid molecules which code for a cadherin-11 polypeptide having the amino acid sequence of SEQ ID NO: 2, but which may differ from the sequence of SEQ ID NO: 1 due to the degeneracy of the genetic code. Similarly, the cadherin-11 modulating nucleic acid molecule, and preferably the cadherin-11 inhibitory nucleic acid molecule, may encode cadherin-11 counter-receptor polypeptides and fragments thereof which are soluble or membrane-bound.

In some important embodiments, the nucleic acids which modulate cellular function of cadherin-11 preferably do not encode a cadherin-11 or a cadherin-11 counter-receptor polypeptide or a fragment thereof that is capable of inhibiting binding of cadherin-11 to a cadherin-11 counter-receptor, nor are they antisense molecules that inhibit the transcription or translation of the foregoing nucleic acid molecules.

The cadherin-11 modulating nucleic acid molecules of the invention can be identified by conventional techniques, e.g., by identifying nucleic acid sequences which code for cadherin-11 polypeptide and which hybridize to a nucleic acid molecule having the sequence of SEQ ID NO: 1 under stringent conditions. The term "stringent conditions", as used herein, refers to parameters with which the art is familiar. More specifically, stringent conditions, as used herein, refer to hybridization at 65° C. in hybridization buffer (3.5×SSC, 0.02% formamide, 0.02% polyvinyl pyrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7; SDS is sodium dodecyl sulphate; and EDTA is ethylenediaminetetraacetic acid. After hybridization, the membrane to which the DNA is transferred is washed at 2×SSC at room temperature and then at 0.1×SSC/0.1×SDS at 65° C.

There are other conditions, reagents, and so forth which can be used, which result in a similar degree of stringency. The skilled artisan will be familiar with such conditions and, thus, they are not given here. It will be understood, however, that the skilled artisan will be able to manipulate the conditions in a manner to permit the clear identification of homologs and alleles of the nucleic acid molecules of the invention. The skilled artisan also is familiar with the methodology for screening cells and libraries for the expression of molecules, such as cadherin-11 inhibitory nucleic acid molecules, which can be isolated and sequenced. In screening for cadherin-11 sequences for example, a Southern blot may be performed using the foregoing conditions, together with a radioactive probe. After washing the membrane to which the DNA is finally transferred, the membrane can be placed against x-ray film to detect the radioactive signal.

In general, cadherin-11 homologs and alleles typically will share at least 70% nucleotide identity with SEQ. ID. NO: 1; and in some instances, will share at least 75% nucleotide identity; and in still other instances, will share at least 80% nucleotide identity. Watson-Crick complements of the foregoing nucleic acids are also embraced by the invention. The preferred cadherin-11 homologs have at least 85% sequence homology to SEQ. ID. NO: 1. More preferably the cadherin-11 homologs have at least 90% and most preferably at least 95% sequence homology to SEQ. ID. NO: 1. The homology can be calculated using various, publicly available software tools developed by NCBI (Bethesda, Md.) that can be obtained through the internet at the ncbi website. Exemplary tools include the BLAST system available at the ncbi website. Pairwise and ClustalW alignments (BLOSUM30 matrix setting) as well as Kyte-Doolittle hydropathic analysis can be obtained using the MacVetor sequence analysis software (Oxford Molecular Group).

The invention also includes degenerate nucleic acids which include alternative codons to those present in the naturally occurring nucleic acid that encodes, for example, the human cadherin-11 polypeptide. As is well known in the art, and as an example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide codons may be employed to direct the protein synthesis apparatus, in vitro or in vivo, to incorporate a serine residue. Similarly, nucleotide sequence triplets which encode other amino acid residues include, but are not limited to, CCA, CCC, CCG and CCT (proline codons); CGA, CGC, CGG, CGT, AGA and AGG (argirine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences.

It should be understood that homologs and alleles and degenerates of nucleic acid molecules coding for a cadherin-11 counter-receptor are also embraced by the invention and can be identified using the same types of techniques and procedures described herein in reference to the cadherin-11 homologs and alleles and degenerates of nucleic acid molecules coding for a cadherin-11.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

The nucleic acid molecule of the invention (e.g., cadherin-11 inhibitory nucleic acid molecule), in one embodiment, is operably linked to a gene expression sequence which directs the expression of the cadherin-11 inhibitory nucleic acid molecule within a eukaryotic cell. The "gene expression sequence" is any regulatory nucleotide sequence, such as a promoter sequence or promoter-enhancer combination which facilitates the efficient transcription and translation of the cadherin-11 inhibitory nucleic acid molecule to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined cadherin-11 inhibitory nucleic acid molecule. The gene expression sequences optionally includes enhancer sequences or upstream activator sequences as desired.

The invention intends to embrace nucleic acid molecules which code for cadherin-11 polypeptides and fragments thereof, cadherin-11 counter-receptor polypeptides and fragments thereof, and cadherin-11 inhibitory agents as described herein. These nucleic acid molecules may be used in both in vivo treatment methods or in vitro screening assays. When expression of the nucleic acid is preferred (as opposed to some embodiments of antisense treatment methods), the nucleic acid molecule is linked to a gene expression sequence which permits expression of the nucleic acid molecule. Nucleic acid molecules of the invention may be introduced into a cell in vitro, followed by the transfer of the cell to the site of inflammation. The cell into which the nucleic acid molecule is introduced may be harvested from the site of inflammation (e.g., a lymphocyte, such as a T cell, a synovioctye, such as a type B synovioctye, a mast cell, a macrophage, a dendritic cell, a plasma cell, a synovial-derived fibroblast, a synovial membrane lining cell, an osteoblast, a cartilage-derived cell or an invasive pannus-derived cell) or it may be a cell which is not normally present at the site of inflammation. A sequence which permits expression of the nucleic acid in a cell located in a joint, such as for example, a synoviocyte, is one which is selectively transcriptionally active in the cell and thereby causes the expression of the nucleic acid in such a cell. Those of ordinary skill in the art will be able to easily identify alternative promoters that are capable of expressing such a nucleic acid molecule in a synoviocte, an osteoblast, a cartilage-derived cell, a lymphocyte or any other cell type mentioned herein. Alternatively, the transduced cell may be cultured in vitro in order to produce a cadherin-11 modulating agent (e.g., cadherin-11 inhibitory agent) or it may be used in in vitro screening assays. For example, the gene expression sequence may be used to express a cadherin-11 nucleic acid molecule in a cell which does not inherently express cadherin-11. The cadherin-11 nucleic acid molecule may also be expressed in a cell which inherently expresses neither cadherin-11 nor cadherin-11 counter-receptor.

The nucleic acid molecule sequences of the invention (e.g., cadherin-11 inhibitory nucleic acid molecules) and the gene expression sequence are said to be "operably linked" when they are covalently linked in such a way as to place the transcription and/or translation of the nucleic acid molecule sequence (e.g., a cadherin-11 coding sequence) under the influence or control of the gene expression sequence. If it is desired that nucleic acid molecule be translated into a functional protein, two DNA sequences are said to be operably linked if induction of a promoter in the 5' gene expression sequence results in the transcription of the nucleic acid molecule and if the nature of the linkage between the two DNA sequences does not (1) result in the introduction of a frame-shift mutation, (2) interfere with the ability of the promoter region to direct the transcription of the nucleic acid molecule, or (3) interfere with the ability of the corresponding RNA transcript to be translated into a polypeptide. Thus, a gene expression sequence would be operably linked to a nucleic acid molecule if the gene expression sequence were capable of effecting transcription of that nucleic acid molecule such that the resulting transcript might be translated into the desired polypeptide.

In still other embodiments, the cadherin-11 modulating agent is a nucleic acid molecule that, rather than encoding a polypeptide, functions as an antisense molecule. Antisense oligonucleotides that selectively bind to a nucleic acid molecule encoding a cadherin-11 polypeptide, or a fragment thereof, or a cadherin-11 counter-receptor (e.g., an integrin or one or more of its subunits), or a fragment thereof, to decrease cadherin-11 mediated adhesion are embraced by the present invention. When using antisense preparations of the invention, local administration to the synovium or synovial fluid is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med* 1(11):1116-1118, 1995). Most preferably, the antisense oligonucleotides comprise a complementary sequence of 20-30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although SEQ ID NO:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO:1. Similarly, antisense to allelic or homologous cadherin-11 or alternatively, cadherin-11 counter-receptor cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acids encoding cadherin-11 or cadherin-11 counter-receptor polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient.

The nucleic acids of the invention can be delivered to, for example, the synovium and to cells of the joint alone or in association with a vector. In its broadest sense, a "vector" is any vehicle capable of facilitating: (1) delivery of a nucleic acid molecule to a target cell and/or (2) uptake of a nucleic acid molecule by a target cell. Preferably, the vectors transport the cadherin-11 modulating nucleic acid molecule into the target cell with reduced degradation relative to the extent of degradation that would result in the absence of the vector. Optionally, a "targeting ligand" can be attached to the vector to selectively deliver the vector to a cell which expresses on its surface the cognate receptor for the targeting ligand. In this manner, the vector (containing, for example, a cadherin-11 inhibitory nucleic acid molecule) can be selectively delivered to the synovial lining in a joint capsule. Methodologies for targeting include conjugates, such as those described in U.S. Pat. No. 5,391,723. Preferably, the nucleic acid molecules of the invention are targeted for delivery to a cell located in a joint capsule, such as a synoviocyte or a lymphocyte.

In general, the vectors useful in the invention are divided into two classes: biological vectors and chemical/physical vectors. Biological vectors are useful for delivery/uptake of nucleic acids to/by a target cell. Biological vectors include, but are not limited to, plasmids, phagemids, viruses, other vehicles derived from viral or bacterial sources that have been manipulated by the insertion or incorporation of the nucleic acid sequences of the invention, and additional nucleic acid fragments (e.g., enhancers, promoters) which can be attached to the nucleic acid sequences of the invention. Viral vectors are a preferred type of biological vector and include, but are not limited to, nucleic acid sequences from the following viruses: adenovirus; adeno-associated virus; retrovirus, such as moloney murine leukemia virus; harvey murine sarcoma virus; murine mammary tumor virus; rouse sarcoma virus; SV40-type viruses; polyoma viruses; Epstein-Barr viruses; papilloma viruses; herpes virus; vaccinia virus; polio virus; and RNA virus such as a retrovirus. One can readily employ other vectors not named but known in the art.

A particularly preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hemopoietic cells, and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman C.O., New York (1990) and Murry, E. J. Ed. "Methods in Molecular Biology," vol. 7, Humana Press, Inc., Cliffton, N.J. (1991). Another preferred retroviral vector is the vector derived from the moloney murine leukemia virus, as described in Nabel, E. G., et al., *Science*, v. 249, p. 1285-1288 (1990).

In addition to the biological vectors, chemical/physical vectors are useful for delivery/uptake of nucleic acids or polypeptides to/by a target cell. As used herein, a "chemical/physical vector" refers to a natural or synthetic molecule, other than those derived from bacteriological or viral sources, capable of delivering the cadherin-11 modulating agent to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µM can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue, by coupling the liposome to a specific ligand such as a monoclonal antibody, sugar, glycolipid, or protein specific for the particular tissue or cell type (e.g., synoviocyte-specific surface proteins). Additionally, the vector may be coupled to a nuclear targeting peptide, which will direct the cadherin-11 modulating nucleic acid molecule to the nucleus of the host cell.

Liposomes are commercially available from Gibco BRL, for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235-241 (1985).

In general, the cadherin-11 modulating nucleic acid molecules can be administered to the subject (any mammalian recipient) using the same modes of administration that currently are used for gene therapy in humans (e.g., adenovirus-mediated gene therapy). A patented procedure for performing ex vivo gene therapy is outlined in U.S. Pat. No. 5,399,346 and in exhibits submitted in the file history of that patent, all of which are publicly available documents. In general, ex vivo gene therapy involves introduction in vitro of a functional copy of a gene or fragment thereof into a cell(s) of a subject and returning the genetically engineered cell(s) to the subject. The functional copy of the gene or fragment thereof is under operable control of regulatory elements which permit expression of the gene in the genetically engineered cell(s). Accordingly, the nucleic acids of the invention, including the cadherin-11 inhibitory nucleic acid molecules, can be delivered to synoviocytes or lymphocytes or other cells of the joint capsule ex vivo or in vivo, to treat an inflammatory joint disorder. Numerous transfection and transduction techniques as well as appropriate expression vectors are well known to these of ordinary skill in the art, some of which are described in PCT application WO95/00654.

As an illustrative example, a vector containing a nucleic acid molecule is delivered to a site of joint inflammation in a subject who is a candidate for such gene therapy. Then, the vector genetically modifies the synoviocytes, osteoblasts, hemopoietic cells such as macrophages and NK cells, and/or lymphocytes in vivo with DNA encoding, for example, a cadherin-11 inhibitory polypeptide of the invention. Such genetically modified joint cells are expected to interfere with cadherin-11 binding to its counter-receptor in vivo.

In an alternative embodiment, primary human synoviocytes can be obtained from a subject who is a candidate for such gene therapy. Then, such cells can be genetically engineered ex vivo with DNA encoding, for example, a cadherin-11 inhibitory polypeptide of the invention. Such recombinant cells are expected to inhibit cadherin-11 mediated adhesion in vivo. In yet another example, another cell type which expresses neither cadherin-11 nor cadherin-11 counter-receptor can be genetically manipulated in vitro to express a cadherin-11 inhibitory agent and then introduced into the site of inflammation.

Exemplary compositions that can be used to facilitate in vitro uptake of the nucleic acid molecules by a target cell include calcium phosphate and other chemical mediators of intracellular transport, microinjection compositions, electroporation and homologous recombination compositions (e.g., for integrating a nucleic acid into a preselected location within the target cell chromosome).

The invention also provides isolated unique fragments of an isolated nucleic acid molecule selected from the group consisting of SEQ ID NO:1. A unique nucleic acid fragment is one that is a 'signature' for the larger nucleic acid. For example, the unique fragment is long enough to assure that its precise sequence is not found in molecules within the human genome outside of the cadherin-11 nucleic acid molecules defined herein. Those of ordinary skill in the art may apply no more than routine procedures to determine if a fragment is unique within the human genome.

The invention further provides a pharmaceutical composition (i.e., a pharmaceutical preparation) for modulating a cadherin-11 mediated function in a subject. The composition includes a pharmaceutically acceptable carrier and a cadherin-11 modulating agent (e.g., a cadherin-11 inhibitory agent).

The pharmaceutical preparations, as described above, are administered in effective amounts. For therapeutic applications, it is generally that amount sufficient to achieve a medically desirable result. In general, a therapeutically effective amount is that amount necessary to delay the onset of, inhibit the progression of, or halt altogether the particular condition being treated. As an example, the effective amount is generally that amount which serves to alleviate the symptoms (e.g., pain, inflammation, etc.) of the disorders described herein. The effective amount will depend upon the mode of administration, the particular condition being treated and the desired outcome. It will also depend upon the stage of the condition, the severity of the condition, the age and physical condition of the subject being treated, the nature of concurrent therapy, if any, the duration of the treatment, the specific route of administration and like factors within the knowledge and expertise of the medical practitioner. For prophylactic applications, it is that amount sufficient to delay the onset of, inhibit the progression of, or halt altogether the particular condition being prevented, and may be measured by the amount required to prevent the onset of symptoms.

Generally, doses of active compounds of the present invention would be from about 0.01 mg/kg per day to 1000 mg/kg per day, preferably from about 0.1 mg/kg to 200 mg/kg and most preferably from about 0.2 mg/kg to about 20 mg/kg, in one or more dose administrations daily, for one or more days. It is expected that doses ranging from 1-500 mg/kg, and preferably doses ranging from 1-100 mg/kg, and even more preferably doses ranging from 1-50 mg/kg, will be suitable. The preferred amount can be determined by one of ordinary skill in the art in accordance with standard practice for determining optimum dosage levels of the agent. It is generally preferred that a maximum dose of a cadherin-11 modulating agent that is the highest safe dose according to sound medical judgement be used.

The cadherin-11 modulating agents of the invention can be administered to a subject in need of such treatment in combination with concurrent therapy for treating an inflammatory joint disorder. The concurrent therapy may be invasive, such as a removal of fluid from the joint capsule, or may involve drug therapy such as the administration of nonsteroidal anti-inflammatory drugs, anti-rheumatic drugs (e.g., gold and penicillamine), immune modulating drugs (e.g., cyclosporin) and corticosteroid drugs. These drug therapies are well-known to those of ordinary skill in the art and are administered by modes known to those of such skill. The drug therapies are administered in amounts which are effective to achieve the physiological goals (e.g., to reduce inflammation in a joint), in combination with, for example, the cadherin-11 inhibitory agent of the invention. Thus, it is contemplated that the drug therapies may be administered in amounts which are not capable of preventing or reducing the physiological consequences of an inflammatory joint disorder when the drug therapies are administered alone but which are capable of reducing the consequences when administered in combination with the cadherin-11 modulating agents of the invention.

The cadherin-11 modulating agent may be administered alone or in combination with the above-described drug therapies as part of a pharmaceutical composition. Such a pharmaceutical composition may include the cadherin-11 modulating agent in combination with any standard physiologically and/or pharmaceutically acceptable carriers which are known in the art. The compositions should be sterile and contain a therapeutically effective amount of the cadherin-11 modulating agent in a unit of weight or volume suitable for administration to a patient.

The term "pharmaceutically-acceptable carrier" as used herein means one or more compatible solid or liquid filler, diluents or encapsulating substances which are suitable for administration into a human or other animal. The term "pharmaceutically acceptable" means a non-toxic material that does not interfere with the effectiveness of the biological activity of the active ingredients. Pharmaceutically acceptable further means a non-toxic material that is compatible with a biological system such as a cell, cell culture, tissue, or organism. The term "carrier" denotes an organic or inorganic ingredient, natural or synthetic, with which the active ingredient is combined to facilitate the application. The characteristics of the carrier will depend on the route of administration. The components of the pharmaceutical compositions also are capable of being commingled with the agents of the present invention, and with each other, in a manner such that there is no interaction which would substantially impair the desired pharmaceutical efficacy. The pharmaceutically acceptable carrier must be sterile for in vivo administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the cadherin-11 modulating agents, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. In preferred embodiments, the pharmaceutical composition is administered directly to the synovium, synovial fluid or joint capsule by injection preferably with a syringe.

Formulations for use in accordance with the methods of the invention include a syringe containing a cadherin-11 modulating agent, such as a cadherin-11 inhibitory agent, and a pharmaceutically acceptable carrier that is suitable for injection into the synovial fluid.

The pharmaceutical compositions may conveniently be presented in unit dosage form and may be prepared by any of the methods well-known in the art of pharmacy. All methods include the step of bringing the cadherin-11 modulating agents into association with a carrier which constitutes one or more accessory ingredients. In general, the compositions are prepared by uniformly and intimately bringing the cadherin-11 modulating agents into association with a liquid carrier, a finely divided solid carrier, or both, and then, if necessary, shaping the product. Compositions suitable for oral administration may be presented as discrete units, such as capsules, tablets, lozenges, each containing a predetermined amount of the cadherin-11 modulating agent. Other compositions include suspensions in aqueous liquids or non-aqueous liquids such as a syrup, elixir or an emulsion.

In one particular embodiment, the preferred vehicle for delivery of the cadherin-11 modulating agents of the invention is a biocompatible microparticle or implant that is suitable for implantation into a joint or in the vicinity of an afflicted joint in the recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the subject. In accordance with the instant invention, the cadherin-11 modulating agents described herein are encapsulated or dispersed within the biocompatible, preferably biodegradable polymeric matrix disclosed in PCT/US/03307. The polymeric matrix preferably is in the form of a microparticle such as a microsphere (wherein, for example, the cadherin-11 inhibitory agent is dispersed throughout a solid polymeric matrix) or a microcapsule (wherein, for example, the cadherin-11 inhibitory agent is stored in the core of a polymeric shell). Other forms of the polymeric matrix for containing the cadherin-11 modulating agent include films, coatings, gels, implants, and stents. The size and composition of the polymeric matrix device is selected to result in favorable release kinetics in the tissue into which the matrix device is implanted. The size of the polymeric matrix devise is further selected according to the method of delivery which is to be used, typically injection into a tissue, such as the joint, joint capsule, synovial membrane or synovial fluid, or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to the synovium of a joint. The matrix composition also can be selected not to degrade, but rather, to release by diffusion over an extended period of time.

Both non-biodegradable and biodegradable polymeric matrices can be used to deliver the cadherin-11 modulating agents, including the cadherin-11 inhibitory agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the cadherin-11 modulating agents of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels (described by H. S. Sawhney, C. P. Pathak and J. A. Hubell in Macromolecules, 1993, 26, 581-587, the teachings of which are incorporated herein), polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl mmethacrylate), poly(phenyl methacrylate), poly(methyl acrylate), poly(isopropyl acrylate), poly(isobutyl acrylate), and poly(octadecyl acrylate).

Examples of non-biodegradable polymers include ethylene vinyl acetate, poly(meth)acrylic acid, polyamides, copolymers and mixtures thereof.

Other delivery systems can include time-release, delayed release or sustained release delivery systems. Such systems can avoid repeated administrations of the cadherin-11 modulating agents described above, increasing convenience to the subject and the physician. Many types of release delivery systems are available and known to those of ordinary skill in the art. They include the above-described polymeric systems, as well as polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and triglycerides; hydrogel release systems; silastic systems; peptide based systems; wax coatings; compressed tablets using conventional binders and excipients; partially fused implants; and the like. Specific examples include, but are not limited to: (a) erosional systems in which the cadherin-11 modulating agent is contained in a form within a matrix such as those described in U.S. Pat. Nos. 4,452,775, 4,675,189 and 5,736, 152 and (b) diffusional systems in which an active component permeates at a controlled rate from a polymer such as described in U.S. Pat. Nos. 3,854,480, 5,133,974 and 5,407, 686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Another aspect of the invention includes a screening assay method for determining whether a putative cadherin-11 inhibitory agent modulates cadherin-11 mediated adhesion. In certain embodiments, an in vitro adhesion assay is used as a screening assay to measure the ability of an agent, e.g., a pharmaceutical lead compound, an antibody or a fragment thereof, a library member or a peptide analog, to inhibit cadherin-11-mediated adhesion between a first cell expressing cadherin-11 and a second cell expressing a cadherin-11 counter-receptor in vitro. The assay is predictive of the ability of the agent to inhibit cadherin-11 mediated activity in vivo.

The binding partners in the adhesion assays are the particular ligands and receptors involved in cadherin-11 mediated adhesion. Accordingly, adhesion assays can be performed in which the binding partners are: (1) a cell expressing a cadherin such as cadherin-11 (e.g., synoviocytes, synovial-derived fibroblasts, osteoblasts and cadherin-11 transfected cells) and a cell expressing a cadherin-11 counter-receptor (e.g., synoviocytes, synovial-derived fibroblasts, osteoblasts, T and B lymphocytes, plasma cells, macrophages, dendritic cells, mast cells, NK cells and cadherin-11 counter-receptor transfected cells; (2) an isolated cadherin-11 and a cell expressing the counter-receptor (3) an isolated cadherin-11 counter-receptor and a cell expressing cadherin-11 and; (4) an isolated cadherin-11 polypeptide and its isolated counter-receptor. When isolated cadherin-11 or an isolated cadherin-11 counter-receptor are used, these may be present in immobilized form (e.g., immobilized on a solid surface) or in soluble form.

As used herein with respect to adhesion assays, a cadherin-11 counter-receptor can be present as an isolated cadherin-11 counter-receptor, a functionally equivalent peptide fragment or analog of the isolated cadherin-11 counter-receptor, or a cell expressing the counter-receptor extracellularly or its functionally equivalent peptide fragment or analog. Similarly, cadherin-11 can be present as an isolated cadherin-11 polypeptide, a functionally equivalent peptide fragment or analog of cadherin-11, or a cell expressing cadherin-11 extracellularly or its functionally equivalent peptide fragment or analog. Cadherin-11 or its counter-receptor can be immobilized on supports, such as microtiter plates or beads, using procedures known to the artisan of ordinary skill in the art.

Thus, a high throughput screening assay for selecting pharmaceutical lead compounds can be performed in which, for example, (1) cadherin-11 or the cadherin-11 counter-receptor is immobilized onto the surface of a microtiter well, (2) aliquots of a molecular library containing library members are added to the wells, (3) cells expressing a cadherin-11 counter-receptor or cadherin-11 (as the case may be) are added to the wells and (4) the well components are allowed to incubate for a period of time that is sufficient for the cells to bind to the immobilized cadherin-11. Preferably, the cells are labeled (e.g., preincubated with $^{51}Cr$ or a fluorescent dye) prior to their addition to the microtiter well. Following the incubation period the wells are washed to remove non-adherent cells and the signal (attributable to the label on the adhering cells) is determined. A positive control (e.g., no library member present) on the same microtiter plate is used to establish maximal adhesion value. A negative control (e.g., soluble cadherin-11 added to the microtiter well) on the same microtiter plate is used to establish maximal levels of inhibition of adhesion. As an example, cadherin-11 can be immobilized to the surface and the cells added can be T cells. Consistent with other embodiments of the invention, the high throughput screening assay may also use an isolated cadherin-11 and/or cadherin-11 counter-receptor, both of which may be in immobilized or soluble form.

The agents to be screened may be pharmaceutical lead compounds synthesized in molecular libraries. These libraries can yield peptides (i.e., peptide libraries) or small organic or inorganic molecules. The agents to be screened can also be peptide analogs of either cadherin-11 or cadherin-11 counter-receptor. Preferably, the peptide or peptide analog of cadherin-11 or cadherin-11 counter-receptor corresponds to the portion of either polypeptide responsible for binding with its binding partner. For both polypeptides, this portion is extracellular.

According to yet another aspect of the invention, a method is provided for screening a molecular library to identify pharmaceutical lead molecules which inhibit the in vitro adhesion between a first cell that expresses cadherin-11 and a second cell that expresses a cadherin-11 counter receptor. For example, the ability of a molecule to inhibit the binding of a synovial cell to a T-lymphocyte or the binding of a synovial cell to another synovial cell in vitro can be used as a screening assay to identify lead compounds which inhibit the binding of cadherin-11 to its counter-receptor. Such adhesion assays are well known in the art and are illustrated by the assay provided in the Examples.

A preferred screening method involves performing an adhesion assay between a first cell and a second cell in the presence and absence of at least one member of the molecular library to determine whether the library member modulates adhesion between the first cell and the second cell in vitro. Preferably the first cell expresses cadherin-11 and the second cell expresses a cadherin-11 counter-receptor. This embodiment involves: (1) performing a first adhesion assay between the first cell and the second cell to obtain a first adhesion assay result; (2) performing a second adhesion assay between the first cell and the second cell in the presence of the library member to obtain a second adhesion assay result; and (3) comparing the first and the second adhesion assay results to determine whether the library member modulates adhesion between the first cell and the second cell. A difference between the first and the second adhesion assay result indicates the ability of the library member to modulate binding between the first cell and the second cell and thus binding of cadherin-11 to its counter-receptor. Thus, for example, an adhesion assay result which shows reduced binding between the first cell and the second cell when the assay is conducted in the presence of the library member, compared to the assay result obtained when the assay is performed in the absence of the library member, indicates that the library member inhibits binding of the first cell and the second cell. An exemplary adhesion assay is provided in the Examples. Other such adhesion assays are well known in the art and can be developed and performed using no more than routine experimentation. Thus, for example, the adhesion assay can be performed by substituting the first cell and the second cell with an isolated cadherin-11 and its isolated counter-receptor.

In yet another aspect, the invention provides a screening assay for pharmaceutical lead compounds which modulate cellular function through cadherin-11. These screening assays involve determining a first value for a cellular parameter (e.g., cell proliferation) of a cadherin-11 expressing cell (e.g., a synoviocyte) in the absence of a molecular library member, determining a second value for the same cellular parameter in a cadherin-11 expressing cell in the presence of a molecular library member, and comparing the first and the second value of the cellular parameter as a measure of the effect of the molecular library member on that particular cellular parameter. As an example, a second value which is lower than the first value is indicative of a reduction in cellular proliferation. Cellular proliferation can be measured in any number of ways, well known to the ordinary artisan, including but not limited to incorporation of radioactive nucleotides (e.g., thymidine uptake assays) and counting of cells. An example of a T cell proliferation assay is described in U.S. Pat. No. 6,077,833, which is incorporated herein in its entirety by reference. In these assays, the cells to be used may be either adhered to a solid surface or may be present in a suspension.

Likewise, the assay can also be carried out by measuring other cellular parameters such as apoptosis, migration, attachment and/or factor (e.g., inflammatory factor) secretion. For apoptosis screening assays, cell counts may be used as a readout of the amount of apoptosis. Other apoptosis assays are described in U.S. Pat. No. 6,107,088. For factor secretion assays, the supernatant within which the cells exist can be tested for the presence of factors, using other functional assays or immunological assays (e.g., ELISA assays, bioassays, western blots, RIA assays, and so forth to detect particular cytokines). For example, secretion of IL-6 can be measured by using the supernatant in an assay measuring cell growth of IL-6 dependent cells. General immune cell activation can also be measured using assays such as those described in U.S. Pat. No. 5,569,585.

In some preferred embodiments, the cellular function is a function other than cadherin-11 binding to a cadherin-11 counter-receptor. Thus, the preferable pharmaceutical lead compound, according to this aspect of the invention, is one which enhances or inhibits a cadherin-11 mediated cellular function such as proliferation, signaling, apoptosis, factor production or secretion, migration or attachment, yet does not inhibit cadherin-11 binding to a cadherin-11 counter-receptor. Preferably, the cadherin-11 modulating agents which do not inhibit cadherin-11 binding to its counter receptor, are selected from small molecule libraries, such as combinational chemistry libraries.

In all of the aforementioned assays, a preliminary binding screen optionally is initially carried out prior to the screening assays described herein. Such a preliminary binding screen would enrich and in some instances identify pharmaceutical lead compounds which bind cadherin-11 or its counter-receptor. These preliminary assays would not necessarily measure the inhibitory or signal modulating capability of the identified compounds, but rather would serve to reduce the number of compounds to be further screened. Thus, as an example, a molecular library may be initially contacted with either (preferably immobilized) cadherin-11 or a cadherin-11 counter-receptor and the library members which bind to cadherin-11 or cadherin-11 counter-receptor would be further screened for their ability to inhibit cadherin-11 binding to its counter-receptor or to modulate cellular function of cadherin-11 expressing cells. Since agents which modulate cellular function do so in cadherin-11 expressing cells, the appropriate preliminary screen for these agents would be binding to cadherin-11. For inhibitory agents of the invention, the preliminary screen may test binding to either cadherin-11 or cadherin-11 counter-receptor.

The cadherin-11 modulating agents of the invention can be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries can be used to develop and select synthetic compounds which are cadherin-11 modulating and/or inhibitory agents. Also envisioned in the invention is the use of agents made from peptoids, random bio-oligomers (U.S. Pat. No. 5,650,489), benzodiazepines, diversomeres such as dydantoins, benzodiazepines and dipeptides, nonpeptidal peptidemimetics with a beta-D-glucose scaffolding, oligocarbamates or peptidyl phosphonates.

The agents of the invention may be produced en masse using library technology. In some aspects, the methods of the invention utilize this library technology to generate and subsequently identify small molecules, including small peptides, which bind to a cadherin-11 or a cadherin-11 counter receptor. One advantage of using libraries is the facile manipulation of millions of different putative candidates of small size in small reaction volumes (i.e., in synthesis and screening reactions). Another advantage of libraries is the ability to synthesize agents which might not otherwise be attainable using naturally occurring sources, particularly in the case of non-peptide moieties.

A "molecular library" refers to a collection of structurally-diverse molecules. Molecular libraries can be chemically-synthesized or recombinantly produced. As used herein, a "molecular library member" refers to a molecule that is present within the molecular library. In general, a molecular library contains from two to $10^{12}$ molecules, and any integer number therebetween, e.g., 2, 3, 4, 5, 10, $10^2$, $10^3$, $10^4$, $10^5$, $10^6$, $10^7$, $10^8$, $10^9$, $10^{10}$, $10^{11}$, $10^{12}$ and so forth, as if each and every integer has been recited herein.

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties which are less subject to enzymatic degradation compared to their naturally-occurring counterparts. Libraries are also meant to include for example but are not limited to peptide on plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Many of these agents of the invention may be synthesized using recombinant or chemical library approaches. A vast array of agents can be generated from libraries of synthetic or natural compounds. Libraries of natural compounds in the form of bacterial, fungal, plant and animal extracts are available or can readily produced. Natural and synthetically produced libraries and compounds can be readily modified through conventional chemical, physical, and biochemical means. Known binding partners of cadherin-11 may be subjected to directed or random chemical modifications such as acylation, alkylation, esterification, amidification, etc. to produce structural analogs of these binding partners, which may function as agonists or antagonists.

Libraries include recombinantly-produced libraries of fusion proteins. An exemplary recombinantly-produced library is prepared by ligating fragments of cadherin-11 cDNA into, for example, the pGEX-2T vector (Pharmacia, Piscataway, N.J.). This vector contains the carboxy terminus of glutathione S-transferase (GST) from *Schistosoma japonicum*. Use of the GST-containing vector facilitates purification of GST-cadherin-11 fusion proteins from bacterial lysates by affinity chromatography on glutathione sepharose. After elution from the affinity column, cadherin-11 GST fusion proteins are tested for activity by, for example, contacting at least one fusion protein with an cadherin-11 expressing cell prior to (or concurrently with) contacting the cadherin-11 counter-receptor expressing cell with a cadherin-11 expressing cell. Fusion proteins which inhibit binding between the cadherin-11 counter-receptor expressing cells and the cadherin-11 expressing cells are selected as pharmaceutical lead compounds. These proteins are also useful in further characterization of the portion of cadherin-11 to which the counter-receptor binds. See, for example, Koivunen E. et al. (1993) J. Biol. Chem. 268(27):20205 which describes the selection of peptides which bind to the $\alpha^5\beta_1$ integrin from a phage display library.

Synthetic DNA and RNA libraries are also commonly used in the art. For instance, Ellington and Szostak describe the use of random polynucleotide libraries to identify novel ligands (Ellington and Szostak, Nature, 346, 818-822 (1990)). As an example, modifications which create variants of cadherin-11 can be made at the level of the nucleic acid sequence which encodes a cadherin-11 polypeptide. Amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of the nucleic acid molecules encoding cadherin-11 or a cadherin-11 counter-receptor.

As described in U.S. Pat. No. 5,908,609, exemplary library compounds also include, but are not limited to, peptides such as, for example, soluble peptides, including but not limited to members of random peptide libraries; (see, e.g., Lam, K. S. et al. 1991, Nature 354:82-84; Houghten, R. et al. 1991, Nature 354:84-86), and combinatorial chemistry-derived molecular libraries made of D- and/or L-configuration amino acids, phosphopeptides (including but not limited to, members of random or partially degenerate, directed phosphopeptide libraries; (see, e.g., Songyang, Z. et al. 1993, Cell 72: 767-778), antibodies (including, but not limited to, polyclonal, monoclonal, humanized, anti-idiotypic, chimeric or single chain antibodies, and FAb, F(ab')$_2$ and FAb expression library fragments (and epitope-binding fragments thereof), and small organic or inorganic molecules. Other compounds which can be screened in accordance with the invention include but are not limited to small organic molecules.

Compounds of the invention that may be designed to satisfy the foregoing criteria include polypeptides and peptide mimetics. The peptide mimetic can be a hybrid molecule which includes both amino acid and non-amino acid components, e.g., the mimic can include amino acid components for the positively charged and negatively charged regions and a non-amino acid (e.g., piperidine) having the same approximate size and dimension of a hydrophobic amino acid (e.g., phenylalanine) as the hydrophobic component.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Thus, the invention provides, in part, low molecular weight compounds that modulate cadherin-11 mediated functions. These compounds can be used to modulate cadherin-11 function or can be used as lead compounds for the design of better compounds using the computer-based rational drug design methods.

One of skill in the art will be familiar with methods for predicting the effect on protein conformation of a change in protein sequence, and can thus "design" a variant which functions as modulating agent according to known methods. One example of such a method is described by Dahiyat and Mayo in Science 278:82-87, 1997, which describes the design of proteins de novo. The method can be applied to a known protein to vary only a portion of the polypeptide sequence. By applying the computational methods of Dahiyat and Mayo, specific variants of cadherin-11 or a cadherin-11 counter-receptor can be proposed and tested to determine whether the variant retains a desired conformation. Similarly, Blake (U.S. Pat. No. 5,565,325) teaches the use of known ligand structures to predict and synthesize variants with similar or modified function.

Other methods for preparing or identifying peptides which bind to a particular target are known in the art. Molecular imprinting, for instance, may be used for the de novo construction of macromolecular structures such as peptides which bind to a particular molecule. See, for example, Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, Trends in Biochem. Sci., 19(9) January 1994; and Wulff, G., in Polymeric Reagents and Catalysts (Ford, W. T., Ed.) ACS Symposium Series No. 308, pp 186-230, American Chemical Society (1986). As an example, one method for preparing mimics of cadherin-11 counter-receptors involves the steps of: (i) polymerization of functional monomers around a known substrate (the template or in this case, cadherin-11 counter-receptor binding domain) that exhibits a desired activity; (ii) removal of the template molecule; and then (iii) polymerization of a second class of monomers in the void left by the template, to provide a new molecule which exhibits one or more desired properties which are similar to that of the template. In addition to preparing peptides in this manner other binding molecules such as polysaccharides, nucleosides, drugs, nucleoproteins, lipoproteins, carbohydrates, glycoproteins, steroids, lipids, and other biologically active materials can also be prepared. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include for example drug design based on structure activity relationships which require the synthesis and evaluation of a number of compounds and molecular modeling.

As mentioned above the invention further embraces agents comprising peptidomimetic residues, including non-naturally occurring amino acids. Such variants can be synthesized by substituting amino acids residues involved in cadherin-11 mediated functions with peptidomimetic residues. For example, glutamine (Glu) residues may be replaced with α-aminoadipate molecules and tyrosine positions may be substituted with 4-carboxymethyl-Phe. Phosphorus and non-phosphorus based analogs, such as phosphorotyrosine mimetics, may be used in the variants. Tyrosine analogs which can be used in place of the tyrosine residues include phenylalanine (Phe), pentafluoro phenylalanine (PfPhe), 4-carboxymethyl-L-phenylalanine (cmPhe), 4-carboxydifluoromethyl-L-phenylalanine ($F_2$cmPhe), 4-phosphonomethyl-phenylalanine (Pmp), (difluorophosphonomethyl)phenylalanine ($F_2$Pmp), O-malonyl-L-tyrosine (malTyr or OMT), and fluoro-O-malonyltyrosine (FOMT). Phosphonate-based mimetics which substitute a methylene unit for the tyrosyl phosphate ester bond may also be incorporated into synthetic agonists and antagonists. Additionally, glutamic acid residues can be modified to possess an additional methylene group or they may simply be substituted with α-aminoadipate (Adi). Other residues which may be used include the non-naturally occurring amino acid 1-aminocyclohexylcarboxylic acid ($Ac_6c$) and 3-(2-hydroxynaphtalen-1-yl)-propyl, or 2-azetidinecarboxylic acid or pipecolic acid (which have 6-membered, and 4-membered ring structures respectively) for proline residues, S-ethylisothiourea, 2-$NH_2$-thiazoline and 2-$NH_2$-thiazole. Also useful in the synthesis of variants is the use of asparagine residue substitutes such as 3-indolyl-propyl. It will be apparent to one of ordinary skill in the art that the invention embraces the synthesis of a wide variety of variants having any combination of amino acid analogs and/or peptidomimetic residues as described above and as are known in the art. Further potential modifications envisioned by the invention include modifications of cysteines, histidines, lysines, arginines, tyrosines, glutamines, asparagines, prolines, and carboxyl groups are well known in the art and are described in U.S. Pat. No. 6,037,134. Synthesis of the afore-mentioned variants is described in the cited references and is well within the realm of one of ordinary skill in the art.

The variants may also be modified to introduce or stabilize certain structural features. As an example, β-bends may be incorporated into the, preferably peptide, variants or the variants may be synthesized as cyclic peptides for example by incorporating thio-ether linkages.

The screening methods of the invention provide useful information for the rational drug design of novel agents which are, for example, capable of modulating an immune system response. Exemplary procedures for rational drug design are provided in Saragovi, H. et al., (1992) Biotechnology 10:773; Haber E., (1983) Biochem. Pharmacol. 32(13):1967; and Connolly Y., (1991) Methods of Enzymology 203, Ch. 29 "Computer-Assisted Rational Drug Design" pp 587-616, the contents of which are incorporated herein by reference.

Thus, knowledge of the primary, secondary or tertiary structures of naturally occurring ligands and receptors can be used to rationally choose or design molecules which will bind with either the ligand or receptor. In particular, knowledge of the binding regions of ligands and receptors can be used to rationally choose or design compounds which are more potent than the naturally occurring ligands in eliciting their normal response or which are competitive inhibitors of the ligand-receptor interaction.

Once rationally chosen or designed and selected, the library members may be altered, e.g., in primary sequence, to produce new and different peptides. These fragments may be produced by site-directed mutagenesis or may be synthesized in vitro. These new fragments may then be tested for their ability to bind to the receptor or ligand and, by varying their primary sequences and observing the effects, peptides with increased binding or inhibitory ability can be produced.

Alternatively, the nucleotide and amino acid sequences of the cadherin-11 modulating agents of the present invention, e.g., those corresponding to the extracellular domain of cadherin-11, may be used in computer-based modeling systems to predict the secondary and tertiary structure of the extracellular domain. Such computer-based systems are well known to those of ordinary skill in the art of rational drug design. Based upon the tertiary structure of a receptor protein, it is often possible to identify a binding region which is involved in its biological activity. From this information, peptides or other compounds which include or mimic this structure and/or which are capable of binding to it can be rationally designed. In this way, new compounds may be designed which mimic the activity of the receptor or ligand or which will act as competitive inhibitors of the receptor or ligand.

It will be appreciated by those skilled in the art that various modifications of the foregoing peptide analogs can be made without departing from the essential nature of the invention. Accordingly, it is intended that peptides which include conservative substitutions and coupled proteins in which a peptide of the invention is coupled to a solid support, such as a polymeric bead, a carrier molecule, such as keyhole limpet hemocyanin, or a reporter group, such as radiolabel or other tag, are also embraced within the teachings of the invention.

As used herein, "conservative amino acid substitution" refers to an amino acid substitution which does not alter the relative charge or size characteristics of the peptide in which the amino acid substitution is made. Conservative substitutions of amino acids include substitutions made amongst amino acids within the following groups: (a) MILV; (b) FYW; (c) KRH; (d) AG; (e) ST; (f) QN; and (g) ED.

The monoclonal antibodies of the invention which inhibit cadherin-11 binding to its counter-receptor also are useful in screening assays for identifying pharmaceutical lead compounds in molecular libraries. The antibodies of the invention specifically bind to a cadherin or a cadherin counter-receptor and thereby inhibit the binding of these two molecules to each other. Thus, screening assays using monoclonal antibodies are also useful for assessing the ability of a library molecule to inhibit the binding of cadherin-11 to its counter-receptor. Such antibody-based screening assays are performed by contacting an antibody (that specifically binds to cadherin-11 and, for example, inhibits adhesion between a T lymphocyte and a cadherin-11 expressing cell) with cadherin-11 in the presence and absence of at least one member of the molecular library and determining whether the library member modulates binding between the antibody and cadherin-11. In a particularly preferred embodiment, cadherin-11 is presented as a cadherin-11-expressing cell, an isolated cadherin-11 or an isolated peptide related to, or derived from, the extracellular domain of cadherin-11. Similarly, the cadherin-11 counter-receptor can be presented in any one of these fashions.

In a particularly preferred embodiment in which the antibody is an anti-cadherin-11 antibody, the antibody screening method involves: (1) performing a first antibody assay in the presence of the antibody and cadherin-11 and in the absence of the library molecule to obtain a first antibody assay result; (2) performing a second antibody assay in the presence of the antibody, cadherin-11 and the library molecule to obtain a second antibody assay result; and (3) comparing the first and the second antibody assay results to determine whether the molecular library member modulates binding between the antibody and cadherin-11. According to this embodiment, reduced binding between the antibody and cadherin-11 in the presence of the library member indicates that the library member has inhibited binding of antibody to cadherin-11. Antibody binding assays also can be used to assess the relative ability of a molecular library member to block binding between an antibody specific for the cadherin-11 counter-receptor and the counter-receptor using no more than routine experimentation.

These and other screening assays can also be used to identify the functionally equivalent cadherin-11 peptide analogs of the invention that are useful for inhibiting the binding of cadherin-11 to its counter-receptor.

The cadherin-11 modulating agents can also be used, for example, to target a toxin (e.g., ricin) or a detectable agent (e.g., a radiolabel, a fluorescent label, an enzyme label) to cells which express cadherin-11 counter-receptors or cadherin-11. Methods for coupling such toxins and/or agents to proteins and/or antibodies for in vivo and in vitro applications are disclosed in, for example, Killen and Lindstrom (1984), "Specific killing of lymphocytes that cause experimental Autoimmune Myestenia Gravis by toxin-acetylcholine receptor conjugates", J. Immun. 133:1335; Jansen, F. K., et al. (1982), "Immunotoxins: Hybrid molecules combining high specificity and potent cytotoxicity", Immunolog. Rev. 62:185-216, the entire contents of which references are incorporated herein by reference. See also U.S. Pat. Nos. 3,652,761; 4,478,946 and 4,554,088, the entire contents of which patents are incorporated herein by reference.

The invention will be more fully understood by reference to the following examples. These examples, however, are merely intended to illustrate the embodiments of the invention and are not to be construed to limit the scope of the invention. It is also to be understood that the reference figures are illustrative only and are not essential to the enablement of the claimed invention.

EXAMPLES

The importance of catenins in mediating cadherin dependent cell-to-cell adhesion suggested that they might be used as probes to identify new cadherins. Thus, for these studies, we obtained antisera to both human α-, and β-catenin and used them to identify co-precipitating proteins in type B human synoviocytes, as this cell type was not known to express a cadherin. In addition, based upon alignments of the human E-, P-, and N-cadherin, four regions of identity can be appreciated. Using these regions we synthesized sense and antisense oligonucleotides and performed PCR under normal stringency conditions using RNA from human type B synoviocytes as the template. The PCR derived clones were then sequenced to identify those that are bonafide cadherin sequences. Such candidate clones were then used as probes in Northern blot analysis using synoviocyte RNA.

Cadherins have not been reported to be expressed in synoviocytes prior to the present invention. The present invention is based, at least in part, on the discovery that synovial derived fibroblast-like cells and synovial membrane lining cells express a cadherin. The gene encoding this cadherin was cloned, monoclonal antibodies were made against it and its expression on transfectant cells, cultured human synoviocytes and in freshly isolated human rheumatoid synovium was demonstrated.

Example 1

Material and Methods:

Antibodies. The P-catenin antisera was previously described (Cepek K L. et al. Proc Natl Acad Sci USA 93:6567-71, 1996). The pan-cadherin antiserum directed against the C-terminal 24 amino acids of chicken N-cadherin was previously described (Geiger B. et al. J Cell Sci 97:607-14, 1990) and obtained from Sigma (St. Louis, Mo.). The specific mouse mAbs against human E-cadherin (E4.6, IgG$_1$) was raised in this laboratory (Cepek K L. et al. Nature 372: 190-3, 1994), the anti-human N-cadherin (13A9, IgG$_1$) was kindly provided by M. Wheelock (Department of Biology, Toledo University, Toledo Ohio), the anti-human VE-cadherin (BV9, IgG$_1$) was a gift from M. G. Lampugnani (Laboratory of Vascular Biology, Mario Negri Institute, Milano, Italy) and the anti-human P-cadherin (NCC-CAD-299, IgG$_1$) was provided by S. Hirohashi (Pathology Division, National Cancer Research Institute, Tokyo, Japan), Leu 4 (anti-CD3) from Becton Dickinson (Mountain View, Calif.), OKT4 (anti-CD4), OKT8 (anti-CD8) from Ortho Pharmaceutical Corp. (Raritan, N.J.), and anti-CD68 from Dako (Carpenteira, Calif.).

Cell Culture. The synovial membranes from RA patients diagnosed based on current criteria (Arnett F C. et al. Arthritis Rheum 31:315-324, 1988) were obtained during hand and wrist synovectomy and joint replacement surgical procedures. Synovial tissue was prepared by mincing and treated with 1 mg/ml collagenase (type 1, Worthington Biochemicals, Frehold, N.J.), 0.15 mg/ml Dnase I (Sigma, St. Louis, Mo.) and 5 nM CaCl$_2$ in phosphate buffer saline (PBS) solution (Gibco, Grand Island, N.Y.), and rocked at 37° C. for 1 hr. The cell suspension was passed through a 40 mesh metal sieve and placed in a 75 cm$^2$ tissue culture flask (BD Labware, Lincoln Park, N.J.). The cells released from the synovial tissue were plated in flasks in DME supplemented with 10% fetal calf and 10% human serum, 2 mM L-glutamine, 1 mM sodium pyruvate, 100 U/ml penicillin, 100 µg/ml streptomycin sulfate, and 50 µM 2-mercaptoethanol and maintained in 10% $CO_2$. Confluent monolayers were found to be composed mainly of the type II (fibroblast like) synoviocytes after the third passage.

The murine fibroblast L-cell line (ATCC CCL1.3) was grown in DMEM, high glucose with 10% bovine calf serum (Hyclone), 10 mM HEPES, 2 mM L-glutamine, 1 mM sodium pyruvate, 10 µM non-essential amino acids (Gibco BRL, Gaithersburg, Md.), 100 U/ml penicillin, 100 µg/ml streptomycin sulfate, and 50 µM 2-mercaptoethanol and maintained in 10% $CO_2$. L-cell transfectants were grown in the above medium with G418 (Gibco) at 1 mg/ml.

Human embryonic kidney HEK293 cells (obtained from ATCC) were maintained in 10% (vol/vol) heat-inactivated FBS (Hyclone Labs Inc., Logan, Utah) and DME medium (Gibco BRL) at 37° C. in 10% $CO_2$.

Cos-7 cells were grown in DMEM, high glucose with 10% Nu-Serum (Collaborative Research, Inc., Bedford, Mass.), 10 mM HEPES, 2 mM L-glutamine, 1 mM sodium pyruvate, 100 U/ml penicillin, 100 µg/ml streptomycin sulfate, and 50 µM 2-mercaptoethanol and maintained in 10% $CO_2$.

Human breast epithelial 16E6.A5 cells were maintained as described (Cepek K L. et al. Proc Natl Acad Sci USA 93:6567-71, 1996).

The T lymphocytes were isolated from Ficoll-Hypaque density gradient derived PMBC using anti-CD3 (or anti-CD2 mAb) and magnetic beads. They may be used directly after release using Detach-a-bead or stimulated with PHA and cultured in IL-2 containing media as long term T cell lines. The isolated fresh lymphocytes will be used in adhesion assays to synovial cell monolayers. Adhesion will be examined in static cell-to-cell assays in 96 well plates using fluorescently labeled lymphocytes. The percentage of fluorescently labeled T cells that bind to synovial cell monolayers is determined using a fluorescence plate reader, and the blocking effects of specific mAb can be determined.

Labeling and Immunoprecipitation. $1 \times 10^7$ confluent synoviocyte monolayers were surface labeled with 2 mCi $Na^{125}I$ (Du Pont-New England Nuclear, Boston, Mass.) using lactoperoxidase and hydrogen peroxide in 0.5 ml PBS as previously described (Brenner, et al. 1987). The cells were solubilized in lysis buffer containing Tris buffered saline (TBS, 50 mM Tris-base, pH 7.6, 140 mM NaCl) with 1% Triton X-100, 8 mM iodoacetamide (IAA) and 1 mM phenylmethylsulfonyl fluoride (PMSF, Sigma, St. Louis, Mo.) 1 mM $CaCl_2$ for 1 hr at 4° C. Detergent insoluble material was removed by centrifugation for 20 minutes at 8,000 g at 4° C. The supernatant was precleared with 6 µl normal rabbit serum and 300 µl 187.1 mAb as culture supernatant for 30 minutes followed by two rounds (1 hr and 12 hrs) of 200 µl of a 10% (wt/vol) cell suspension of fixed *Staphylococcus aureus* Cowen strain I (PANSCORBIN, Calbiochem, San Diego, Calif.). Lysates containing the equivalent of $2 \times 10^6$ cells were immunoprecipitated with 10-15 µl of rabbit antiserum or 15 µl of anti-β catenin antisera or 1 µl of E4.6 ascites, and 100 µl each of 13A9, BV9, Cad-299, 2G4, 5H6, 3H10 mAb supernatants plus 100 µl rat anti-mouse K-chain mAb 187.1 culture supernatant for optimal protein A binding. Immune complexes were then incubated with protein A-Sepharose (Pharmacia Biotechnology Inc., Piscataway, N.J.) for 1 hr at 4° C. with rocking. The immunoprecipitates were washed three times with 0.5% (vol/vol) Triton X-100 in 0.5 M NaCl with 50 mM, 1 mM $CaCl_2$. The resin pellet was boiled in sample buffer (10% glycerol, 3% SDS, 0.5 M Tris, pH 6.8) containing 2-mercaptoethanol (5% final concentration, reducing conditions) and analyzed by 7.5% SDS-PAGE as described (Laemmli UK. Nature 227:680-5, 1970) and subjected to standard fluorographic procedures.

Molecular Cloning of The Gene Encoding the Synovial Cadherin. A number of new cadherin cDNA clones have been isolated using PCR based consensus oligonucleotides corresponding to cytoplasmic domain sequences that are highly conserved among cadherins (Suzuki S. et al. Cell Reg 2:261-70, 1991). Based upon alignments of the human cadherins, four regions of identity can be appreciated, corresponding to human E-cadherin residues 753-762 (EEGGGEEDQD) (SEQ ID NO:3), residues 840-847 (SLSSLNSS) (SEQ ID NO:4), residues 853-859 (QDYDYLN) (SEQ ID NO:5), and residues 865-875 (FKKLADMYGGG) (SEQ ID NO:6), which in each case are identical in E-, P-, and N-cadherins. Using these regions we designed the following degenerate oligonucleotides sense: 5'-GCGGGATCCGAIGARGGIG-GNGGNGA-3' (SEQ ID NO:7) and antisense: 5'GGG-GAGCTCTCIGCIARYTTYTTRAA-3' (N=A,T,G,C; I=Inosine; Y=C,T and R=A,G) (SEQ ID NO:8). mRNA was extracted from rheumatoid synoviocytes and reversed transcribed and used as a template for PCR amplification using 0.5 U/reaction of Taq polymerase and the following conditions: denaturing 95° C. for 30 sec, annealing 60° C. for 1 minute, extension 72° C. for 1 minute during 30 cycles. The PCR products of the expected 385 bp size were cloned into pCRII plasmid using the TA cloning system (Invitrogen Corp., Carlsbad, Calif.) and subsequently sequenced with the Sequenase kit (United Stated Biochemical Corp., Cleveland, Ohio) to identify those that appear to be bonafide cadherin sequences. We searched GenBank database using the FASTA/BLAST program.

Northern Blot. To confirm the expression of the cloned cadherin in synoviocytes we performed northern blot analysis. mRNA isolated from synoviocytes type B, 16A5 cells, Jurkat cells and a SKNSH were hybridized with the 385 bp fragment of the cadherin cloned by PCR and glyceraldehyde-3-phosphate dehydrogenase, as the control, both of which were labeled with [$^{32}$P] dCTP/dGTP by random priming. Hybridization was performed at 43° C. during 16 hrs. After hybridization, the membrane was washed at a final stringency of 0.1×SSC with 2% (w/v) SDS at 56° C. and autoradiographed on Kodak MS film at −70° C.

Construction of Full Length Clone. Full length cadherin-11 was constructed by PCR using the following primers XV14 (5'-CCAAAAATGAAGGAGAACTACT-3') (SEQ ID NO:9) and XV15 (5'-GGGGGATCCATTGTTAA-GAATCGTCATCAAA-3') (SEQ ID NO:10) comprising the coding region of cadherin-1. The product of ~2.4 kb was subcloned into the Hind III/Bam H1 sites of pBluescript SK and sequenced to confirm that no mutations were introduced during the PCR.

Figure 3:
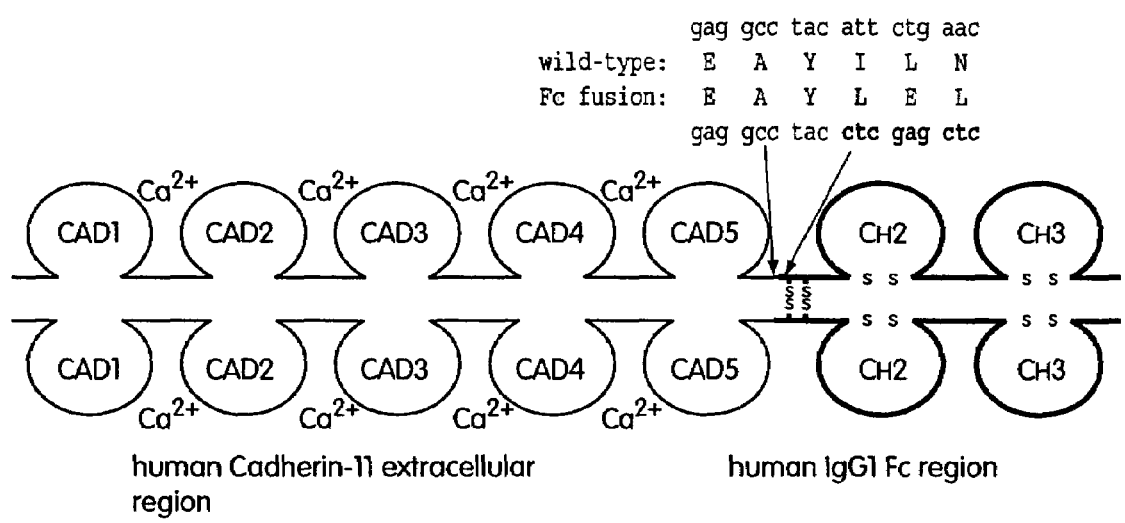
FIG. 3 is a schematic of the structure of the human cadherin-11-Fc fusion protein. The sequence of the extracellular juxtamembrane region of wild-type cadherin-11 (nucleic acid sequence is SEQ ID NO:13; amino acid sequence is SEQ ID NO:14) and the alterations resulting from fusion with the human Fc region (nucleic acid sequence is SEQ ID NO:15; amino acid sequence is SEQ ID NO:16) are shown. Regions corresponding to the Fc portion are shown in bold.

Construction of Cadherin-11-Fc Expression Vector. A double stranded DNA adapter containing a 5' Msc I blunt end, and the final five codons of the human cadherin-11 extracellular region, and a 3' Xho I cohesive end was produced by annealing the complimentary oligonucleotides XVCad11A (5'-GCTGGCACCGTGGTTGGGAGAGT-3') (SEQ ID NO:11) and XVCad11 E (5'-GGGGGGCTCGAGGTAGGC-CTCTGCGTTGCAGG-3') (SEQ ID NO:12) using *Pyrococcus Furiosus* (PFU) (Stratagene, La Jolla, Calif.) according to the manufacturer's recommendations. This adapter was then ligated to the 3'-end of an Hind III-Msc I fragment encoding the rest of the extracellular region of human cadherin-11 from the cadherin-11 full length clone generated previously. The resulting Hind III-Xho I fragment was introduced in frame, upstream of coding for the hinge and Fc region of human IgG$_1$ in a derivative of pCDM8 (pCDM8Fc) also cleaved with Hind III-Xho I. The sequence of the junctional region is shown in FIG. 3. The construct was sequenced to confirm its integrity at the junctional region using an automated DNA sequencer (Perkin Elmer). Finally, the cadherin-11-Fc cDNA was excised from pCDM8 using Hind III and Not I and inserted into the expression vector pCEP4 (Invitrogen Corp. Carlsbad, Calif.) cleaved with Hind III and Not I.

Production of Cadherin-11-Fc Proteins. HEK293 cells (10$^6$ cells per 75 cm$^2$ flask) were stably transfected with 20 μg plasmid DNA using the Mammalian transfection kit (Stratagene). After growth for 24 hrs in nonselective medium, the cells were transferred to 96-well tissue culture plates and incubated in selective medium containing 200 μg/ml hygromycin B. After 15 days, supernatants from wells containing resistant colonies were assayed for fusion proteins by ELISA.

To produce the cadherin-11-Fc protein, positive clones were grown in triple-layer 500-cm$^2$ flasks (Nunc, Roskilde, Denmark) in 10% (v/v) ultralow Ig FBS (GIBCO BRL), 200 μg/ml hygromycin B and DMEM. After 7-10 days of culture, the supernatant was harvested and filtered through a 0.2 μm membrane. The cadherin-11-Fc fusion protein was then purified on a previously unused GammaBind G-Sepharose column (Pharmacia Biotech, Piscataway, N.J.). The column was washed with TBS and 1 mM CaCl$_2$, pH 7.4, and then eluted with 0.2 M glycine and 1 mM CaCl$_2$, pH 2.3. Fractions containing purified fusion protein were dialyzed into TBS and 1 mM CaCl$_2$, pH 7.4 and then stored at −20° C. The purity of the fusion protein was assessed by SDS-PAGE and Coomassie blue staining, and the concentration was determined by Bradford assay using BSA as the standard (BioRad Labs., Hercules, Calif.).

Generation of L-cell-Cadherin-11 Stable Transfectants. To produce cells expressing cadherin-11 in the surface, L-cells were transfected with 20 μg pLK/Cad11 or with the pLK neo vector alone using the Mammalian transfection kit (Stratagene). Then transfected cells were selected by culture in 1 mg/ml G418.

Generation Of Mouse Monoclonal Antibodies Against Cadherin-11. The mAb 2G4, 5H6 and 3H10 were produced by immunizing BALB/c mice with three intraperitoneal injections of 20 μg of purified cadherin-11-Fc. The initial injection was in CFA and the subsequent 2 were in IFA at 2 weeks intervals, followed by a final boost IV of 30 μg. Three days after the intravenous immunization, splenocytes were isolated and fused with NS1 murine myeloma cells in the presence of PEG (MW 1450) as described previously (Lerner E A. Yale J Biol Med 54:387-402. 1981). Hybridomas were selected with aminopterin-containing medium, and hybridoma supernatants were screened by differential ELISA in plates coated with 301-Fc, E-cad-Fc and human IgG$_1$. Subsequent screening was done in the selected clones by FACS in cadherin-11 expressing cells in comparison to E-cadherin positive cells. The selected hybridomas were subcloned thrice by limiting dilution. The isotypes of 2G4 (IgG$_1$), 5H6 (IgG$_1$) and 3H10 (IgG$_1$) were determined by ELISA using murine isotype specific mAb (Jackson Immunoresearch Lab).

Immunohistochemistry. Normal human tissue samples were obtained and snap-frozen in OCT compound (Ames Co., Elkart, Ind.) cooled by liquid nitrogen to about −140° C. Frozen tissue sections were sectioned (6 μm) with a CM 10800 cryostat (Leica Inc. Deerfield, Ill.), and then fixed in acetone for 10 minutes, briefly air-dried, and stained by an indirect immunoperoxidase method using avidin-biotin-peroxidase complex (Vector Labs, Burlingame, Calif.) and 3-amino-9-ethylcarbazole (Sigma, St. Louis, Mo.) as the chromogen.

Results

Figure 2:
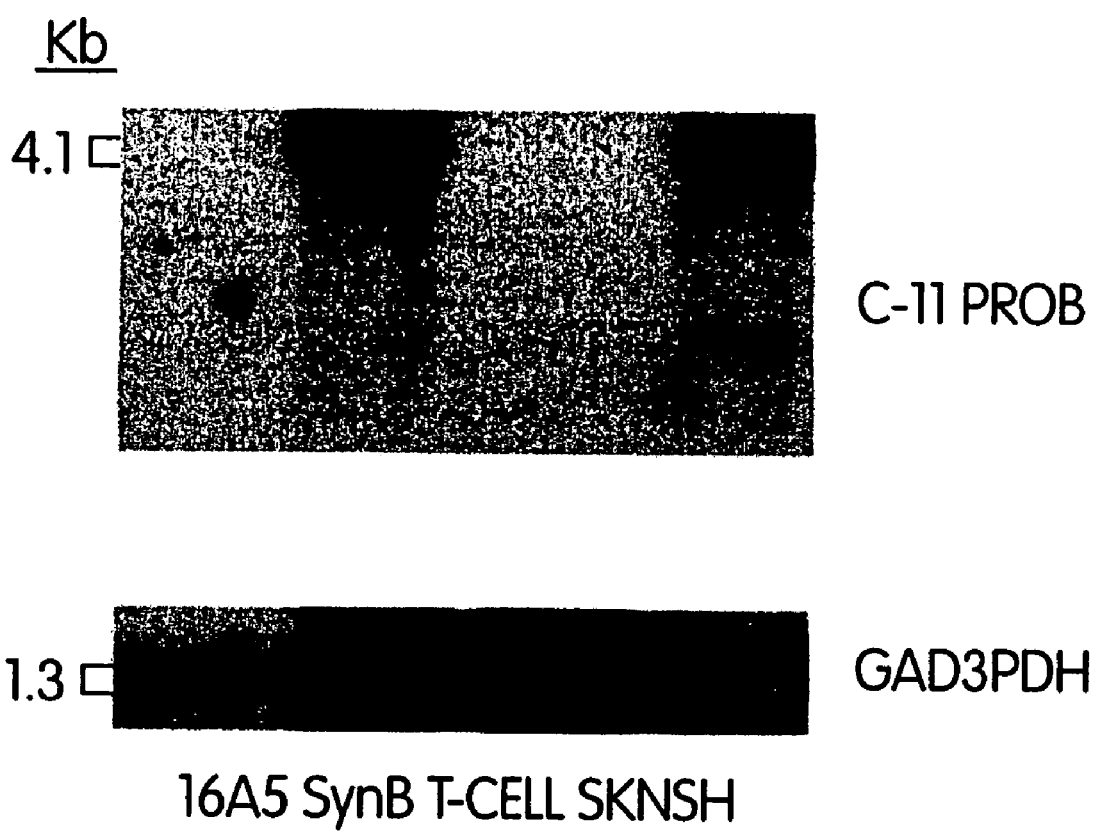
FIG. 2 illustrates results from a Northern analysis of mRNA from 16E6.A5 EpC line (lane 1), type B synoviocytes (lane 2), Jurkat cells (lane 3) and the neuroblastoma cell line SKNSH (lane 4). hybridized with the 385 bp fragment of cadherin-11 (top panel) and a glyceraldehyde-3-phosphate dehydrogenase probe (Clontech) (bottom panel) as a control. The molecular mass markers is indicated on the left.

Cloning of the Synoviocyte Cadherin. The PCR based degenerate oligonucleotide cloning of a cadherin in type B synoviocyte cDNA showed a specific product in synoviocytes that was absent in the negative control (FIG. 1). This product was identified as a fragment of cadherin-11 when sequenced and compared to the GenBank database. We then confirmed the expression of cadherin-11 in synovial derived RNA by Northern blot using as a probe the 385 bp cloned by PCR. FIG. 2 shows the positive hybridization of cad-11 probe in synoviocytes type B and in a positive control, a neuroblastoma cell line (SKNSH) and was absent in epithelial cells (16EA5) and Jurkat cells. In order to obtain the full-length gene we generated a clone comprising the entire coding sequence of human cadherin-11 by PCR. The PCR product obtained was sequenced to confirm lack of mutations.

Production of Human Cadherin-11-Fc Fusion Protein. A construct encoding the extracellular portion of human cadherin-11 was linked in frame to a construct encoding the Fc region of human IgG$_1$ (including the hinge, $C_H2$, and $C_H3$ domains). Transfection of HEK293 cells and selection with hygromycin B led to the generation of stable lines expressing soluble cadherin-11-Fc fusion protein. The cadherin-11-Fc fusion protein was expected to be dimeric due to the presence of disulfide bonds in the (FIG. 3), possibly similar to cadherin dimers on the cell surface (Shapiro L. et al. Nature 374:327-37, 1995; Nagar B M. et al. 380:360-4, 1996). After purification on protein G-Sepharose, SDS-PAGE revealed the presence of a protein of the expected (~123 kD) size after reduction.

Figure 4:
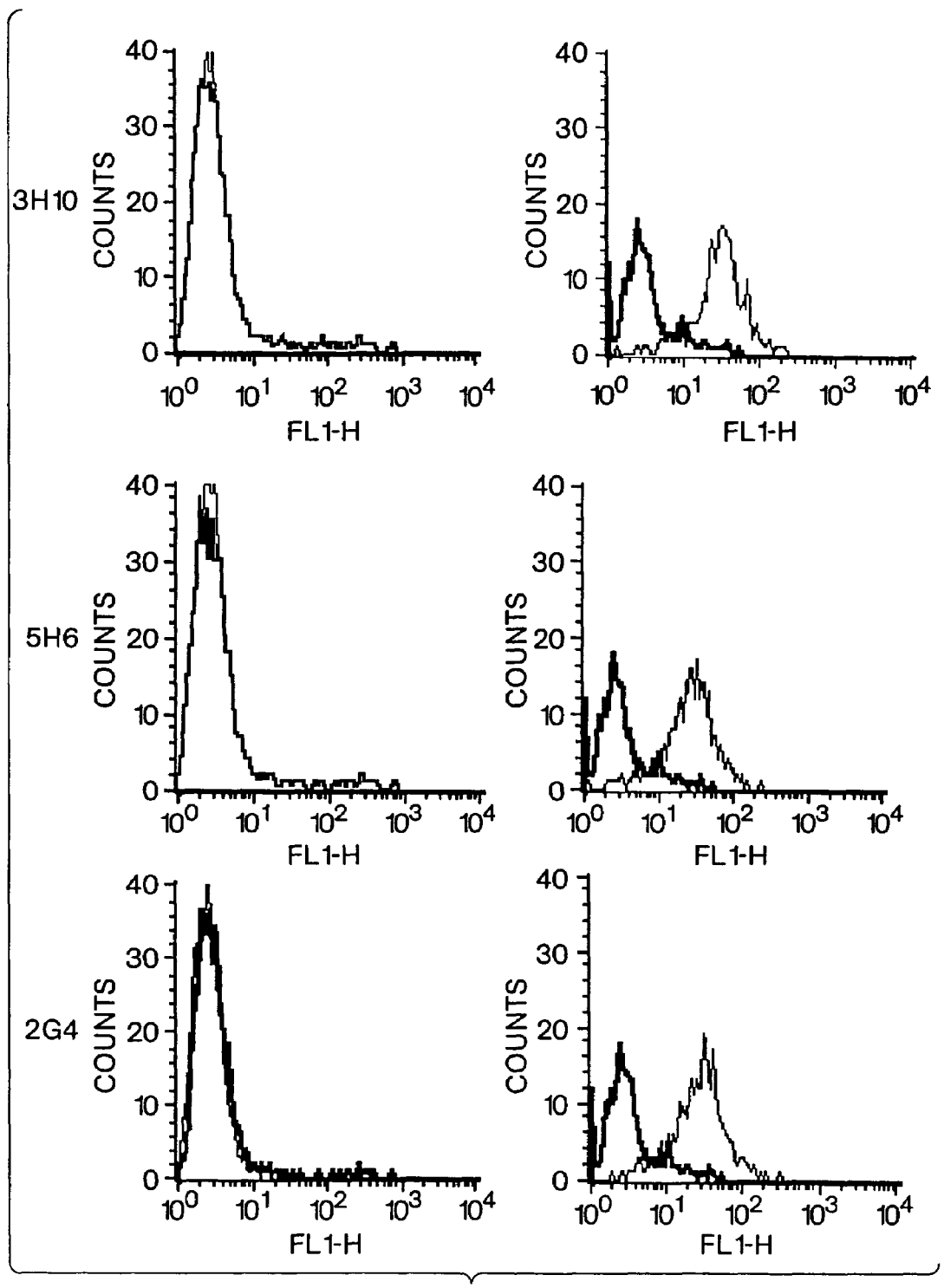
FIG. 4 is a series of flow cytometry histograms showing cell surface expression of cadherin-11 in L-cells transfected with cadherin-11 cDNA. L-cells transfected with pLK-neo (left column) or with pLK-neo/C11 (right column) are shown. Staining with control mAb P3 is shown unshaded. Staining with αCad-11, 3H10, 5H6, and 2G4 is shown shaded.
Figure 5A:
FIG. 5 is a photocopy of a photograph illustrating the immunohistochemistry staining of synovial lining cells and some sublining cells in RA synovitis using mAb 2G4. Frozen tissue sections of human RA synovium (panel A and B) were stained by the indirect immunoperoxidase method using 2G4 mAb and counterstained with hematoxylin (magnification 20× [panel A] and 60× [panel B]). Most of the lining cells and few in the sublining were 2G4+ (panel B).
Figure 5B:
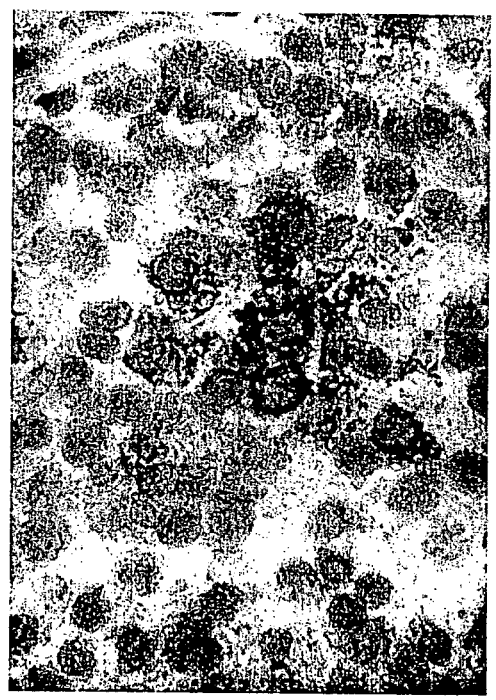

Generation of Anti-Cadherin-11 Monoclonal Antibodies. To produce mAb which specifically recognized the extracellular region of cadherin-11, BALB/c mice were immunized with the purified cadherin-1'-Fc fusion protein. mAb which preferentially reacted with cadherin-11-Fc but not human IgG$_1$ nor E-cadherin-Fc by ELISA were selected for further study. Three of these mAb antibodies 3H10, 5H6 and 2G4 recognized specifically cadherin-11-Fc in ELISA. Also these mAb stain cadherin-11 expressed on the surface of L-cells transfected with full length cadherin-11 as shown in FIG. 4. These three mAb also precipitated a protein of 123 kD from the surface-labeled synoviocytes.

Figure 6:
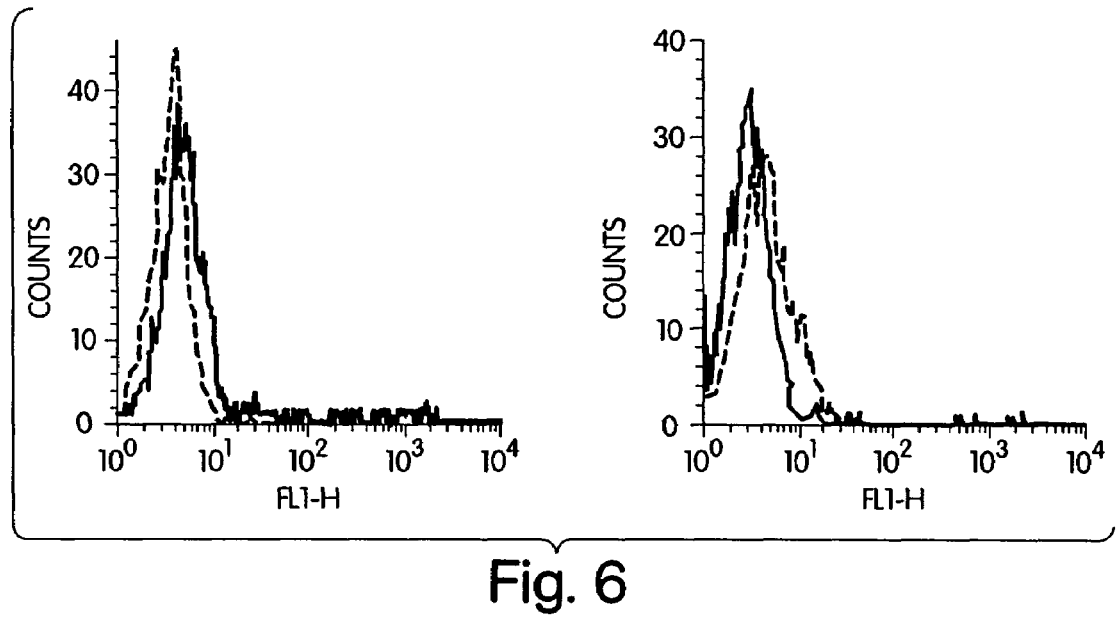
FIG. 6 illustrates a flow cytometric analysis of cadherin-11 expression by synovial T cell line 5 (left panel) and CP-B cells (right panel).

In order to study the pattern of tissue distribution of the protein we performed indirect immunohistochemistry in frozen tissue sections. We noted the remarkable staining pattern in which anti-cadherin-11 mAb preferentially stained the lining cells in RA synovium. This suggests that cadherin-11 plays an important role in determining the adhesion of the synovial lining cells to one another and thereby determining the tissue architecture of the synovium. This role may be critical to the growth and proliferation as well as to the activation of the synovial membrane cells. Note that synovial membranes lack an epithelial layer and instead have the synovial lining layer. Interestingly these anti-cadherin-11 mAb also recognized few cells in the sublining adjacent to the T-cell areas infiltrating the synovium (FIG. 6, panels A and B).

Example 2

Adhesion Assays

Monolayers of adherent cells (i.e., human synoviocytes) were grown in flat bottomed 96-well Linbro tissue culture plates. 10$^4$ adherent cells in 100 μl complete media were added per well and allowed to grow for two to three days until they reached confluence. Just prior to the addition of T cells or cadherin-11 counter-receptor transfected COS 7 cells, the adherent cell monolayers were washed with assay media. To label T cells or COS-7 cells, 25 μg of 2',7'-bis-(2-carboxyethyl)-5 (and -6)-carboxyfluorescein (BCECF-AM, Molecular Probes, Inc., Eugene, Oreg.) was diluted in 5 µl DMSO and added to a suspension of 5×10⁶/ml T cells or COS-7 cells in complete media. The cells were incubated at 37° C. for 25 minutes then washed twice in assay media (PBS containing 1 mM CaCl$_2$, 2 mM MgCl$_2$ and 10 mM HEPES). After washing, 50,000 labeled T cells or COS-7 cells in 100 µl of assay media were added to the adherent cell monolayers. T cells or COS-7 cells were allowed to settle onto adherent cell monolayers for 25 or 40 minutes at 37° C. Unbound cells were removed by flicking media from the plate. Bound cells were detected using a Fluorescence plate reader (IDEXX Co., Portland, Me.). If antibody blocking was performed, the T cells, COS-7 cells, or synoviocyte cell monolayers were pre-incubated with a 1:250 dilution of ascites fluid or 10 µg/ml of purified mAb for five minutes at 37° C. prior to encounter with the second cell type. At least four replicates are performed. The % cells bound is calculated by reading the fluorescence units obtained after unbound cells were washed off, dividing this number by the input fluorescence units and multiplying by 100. Serial dilutions of labeled cells showed that as few as 1000 cells are detected in the linear range.

Example 3

An Adhesion Assay for Selecting Library Members as Pharmaceutical Lead Compounds The adhesion assay described herein is based upon the assay described by Cepek, K., et al., in J. Immunol. 150(8): 3459-3470 (1993), the entire contents of which are incorporated herein by reference.

To screen a molecular library or other mixture for the presence of a functionally equivalent peptide analog or a library member capable of inhibiting cadherin-11 mediated adhesion, T cells are washed with HBSS (Hanks buffered saline solution Gibco) and pre-equilibrated with HBSS containing serial dilutions of the library or other peptide-containing or small molecule-containing solution (over a broad concentration range (e.g., 1 ng/ml to 100 ug/ml) for selected times (e.g., 30 min, 1 hour, 2 hours, 6 hours) at 37° C. before incubation with synovial monolayers that have been washed with HBSS. Functionally equivalent peptide analogs or cadherin-11 inhibitory agents are identified by their ability to inhibit the binding of T cells to the synovial monolayer.

Example 4

Cadherin-11 Counter-Receptor on T and B Cells

Flow cytometric analysis of the synovial T cell line 5 and CP-B cells with anti-cadherin-11 monoclonal antibody 2G4 was performed. Control staining was carried out with the control monoclonal antibody P3. FIG. 6 demonstrates the lack of staining of either the T or the B cell line with the cadherin-11 specific monoclonal antibody.

Figure 7:
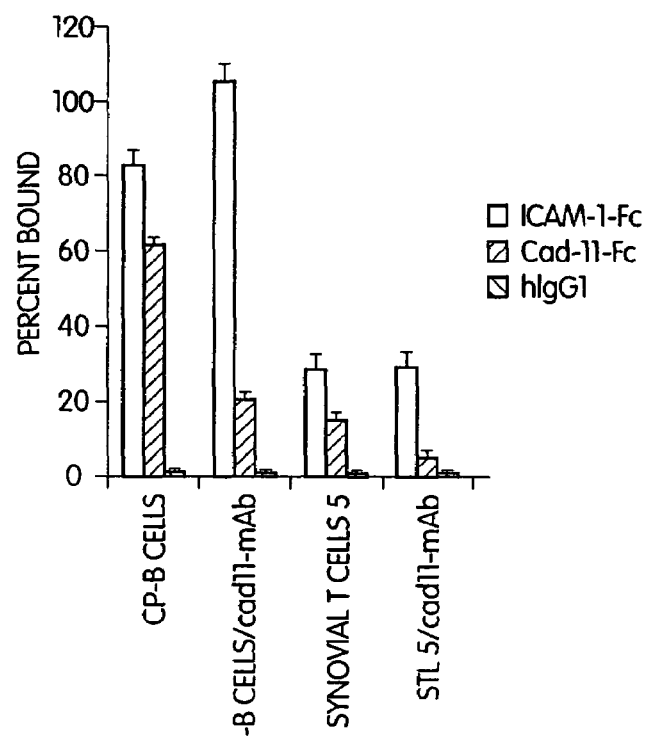
FIG. 7 is a plot of the percent of synovial T cell line 5 cells and CP-B cells bound to control proteins or cadherin-11.

To test the binding of cadherin-11 to T and B cells, the synovial T cell line 5 and CP-B cells were used. Plates were treated with cadherin-11-Fc or ICAM-1-Fc and IgG1. Both cell lines were labeled with a fluorescent dye and were added to the plates and input fluorescence was determined in a fluorescence plate reader. Cells were allow to adhere for 30 minutes at 37° C., subsequently washed and the ratio of bound cells to fluorescence was determined. The percentage of cells bound was determined using the equation: fluorescence after wash/input fluorescence×100. The binding to cadherin-11-Fc but not to control proteins ICAM-1-Fc and IgG1 is blocked by anti-cadherin-11 monoclonal antibody 7D3. The results are expressed as the mean+1 SD (n=4) as shown in FIG. 7.

Several lines of evidence support the possibility that cadherin-11 binds to a counter-receptor expressed on B and T lymphocytes. First, immunohistochemical analysis of RA synovium demonstrated cadherin-11 expression in sublining cells in close contact with lymphocytes. Second, some T cell lines derived from RA synovium and B cells derived from the peripheral blood bind specifically to cadherin-11-Fc and this interaction is blocked by anti-cadherin-11 mAbs. Third, cadherin-11 was not expressed on these leukocyte lines, suggesting that the interaction is not mediated by homophilic but by a heterophilic binding to a cadherin-11 receptor (C11CR) expressed on B and T cells.

Discussion

Here we described for the first time the presence of a cadherin expressed on synoviocytes. Cadherins are expressed on all cells that form solid tissues and are responsible for segregating and sorting cells during tissue morphogenesis. They play a role in establishing cell polarity and maintaining tissue morphology in adult tissues. Although cadherins function classically to mediate homophilic cell-to-cell adhesion, they sometimes bind to nonidentical cadherins or to integrins, such as integrin $\alpha^E\beta_7$.

Our findings of preferential expression of cadherin-11 in the lining of RA synovium suggest that this adhesion molecule could be the key molecule used by the invasive pannus to attach to cartilage and eventually erode into bone, particularly since this cadherin has been reported to be expressed by osteoblasts. This is of particular relevance because we can interfere with the chronic destructive process characteristic of RA if we can modulate the adhesive function of cadherin-11.

We consider the identification of cadherin-11 from human type B synoviocytes an important finding and its tissue distribution within the RA synovium supports its relevant role in invading and eventually eroding the adjacent bone.

It should be understood that the preceding is merely a detailed description of certain preferred embodiments. It therefore should be apparent to those of ordinary skill in the art that various modifications and equivalents can be made without departing from the spirit and scope of the invention. It is intended that the invention encompass all such modifications within the scope of the appended claims.

All references, patents and patent applications and publications that are recited in this application are incorporated in their entirety herein by reference.

We claim:

1. A method for treating a subject having an inflammatory joint disorder comprising
   administering to a subject in need of such treatment a therapeutically effective amount of a cadherin-11 inhibitory agent
   wherein the cadherin-11 inhibitory agent inhibits binding of cadherin-11 to a cadherin-11 counter-receptor that is cadherin-11, and comprises a soluble cadherin-11 polypeptide or a fragment thereof that comprises cadherin-11 extracellular domains 1-5.

2. The method of claim 1, wherein the inflammatory joint disorder is chronic synovitis.

3. The method of claim 1, wherein the inflammatory joint disorder is an autoimmune disease.

4. The method of claim 3, wherein the autoimmune disease is rheumatoid arthritis.

5. The method of claim 1, wherein the cadherin-11 inhibitory agent is administered locally to a synovium of the subject.

6. The method of claim 1, wherein the cadherin-11 inhibitory agent binds to cadherin-11.

7. The method of claim 1, wherein the cadherin-11 inhibitory agent is a soluble cadherin-11 polypeptide.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial sequence
<220> FEATURE:

```
<223> OTHER INFORMATION: Synthetic oligonucleotide
<220> FEATURE:
<221> NAME/KEY: misc_feature
<222> LOCATION: (1)..(18)
<223> OTHER INFORMATION: from Homo sapiens cadherin-11

<400> SEQUENCE: 1
gaggcctaca ttctgaac                                                 18

<210> SEQ ID NO 2
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: from Homo sapiens cadherin-11

<400> SEQUENCE: 2

Glu Ala Tyr Ile Leu Asn
1               5

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
gaggcctacc tcgagctc                                                 18

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Glu Ala Tyr Leu Glu Leu
1               5
```